(12) United States Patent
Cote et al.

(10) Patent No.: US 10,987,035 B2
(45) Date of Patent: Apr. 27, 2021

(54) EYE COUPLING MECHANISM FOR NONINVASIVE GLUCOSE MEASUREMENTS WITH POLARIZED LIGHT

(71) Applicant: TEXAS A & M UNIVERSITY SYSTEM, College Station, TX (US)

(72) Inventors: Gerard Cote, College Station, TX (US); John Hanks, Austin, TX (US); Casey Pirnstill, Bucyrus, OH (US)

(73) Assignee: The Texas A&M University System, College Station, TX (US)

( * ) Notice: Subject to any disclaimer, the term of this patent is extended or adjusted under 35 U.S.C. 154(b) by 510 days.

(21) Appl. No.: 15/683,282

(22) Filed: Aug. 22, 2017

(65) Prior Publication Data
US 2018/0049683 A1    Feb. 22, 2018

Related U.S. Application Data

(60) Provisional application No. 62/377,827, filed on Aug. 22, 2016.

(51) Int. Cl.
*A61B 5/1455*    (2006.01)
*G02B 27/28*    (2006.01)
(Continued)

(52) U.S. Cl.
CPC ...... *A61B 5/14558* (2013.01); *A61B 5/14507* (2013.01); *A61B 5/14532* (2013.01);
(Continued)

(58) Field of Classification Search
None
See application file for complete search history.

(56) References Cited

U.S. PATENT DOCUMENTS 5,209,231 A    5/1993 Cote et al.
6,188,477 B1 *    2/2001 Pu ...................... B82Y 30/00
                                                  356/368

(Continued)

OTHER PUBLICATIONS

Optical Aberation, Wikipedia the free encyclopedia, https://en.wikipedia.org/wiki/Optical_aberration, downloaded Aug. 22, 2017.

*Primary Examiner* — Marjan Fardanesh
(74) *Attorney, Agent, or Firm* — Winstead PC

(57) ABSTRACT

Embodiments concern coupling polarized light at two or more wavelengths across the aqueous humor of the eye (e.g., as part of a noninvasive glucose monitoring system). An approach discloses non-contact and minimal contact eye-coupling designs that are part of a system for providing glucose concentration levels via measurements acquired by passing two or more optical beams through the cornea/aqueous chamber in the eye. The approach provides for coupling the light to account for the index mismatch incurred while allowing for monitoring the light polarization. Specifically, in an embodiment the light transitions from the device, through the air, through the proximal side of the cornea, through the aqueous humor, through the medial side of the cornea, and through the air back into the device. Embodiments address the index of refraction mismatch and polarized light maintaining concerns with a coupling approach that can take the form of contact and non-contact mechanisms.

17 Claims, 15 Drawing Sheets

(51) Int. Cl.
*G02B 26/10* (2006.01)
*G02C 11/00* (2006.01)
*A61B 5/145* (2006.01)
*A61B 5/00* (2006.01)

(52) U.S. Cl.
CPC .......... *A61B 5/6821* (2013.01); *G02B 26/105* (2013.01); *G02B 27/286* (2013.01); *G02C 11/00* (2013.01); *A61B 5/6803* (2013.01)

(56) References Cited

U.S. PATENT DOCUMENTS

| | | | |
|---|---|---|---|
| 6,246,893 B1 * | 6/2001 | Gobeli | A61B 5/14558 600/318 |
| 6,885,882 B2 | 4/2005 | Cote et al. | |
| 2018/0024104 A1 * | 1/2018 | Islam | A61B 5/0088 250/341.1 |

* cited by examiner

EYE COUPLING MECHANISM FOR NONINVASIVE GLUCOSE MEASUREMENTS WITH POLARIZED LIGHT

CROSS-REFERENCE TO RELATED APPLICATION

This application claims priority to U.S. Provisional Patent Application No. 62/377,827 filed on Aug. 22, 2016 and entitled "Eye Coupling Mechanism for Noninvasive Glucose Measurements With Polarized Light", the content of which is hereby incorporated by reference.

BACKGROUND

Diabetes is a huge problem in the US and has more than doubled world-wide since 1980 to over 345 million people. Self-monitoring of blood glucose is recommended for diabetic patients as the current standard of care. There is a need by people with Diabetes to monitor glucose noninvasively and avoid the frequent (up to 5 times daily) finger or forearm pricks required today. There is an unmet need for simple, non-invasive self-glucose monitoring devices for people with both Type 1 insulin dependent diabetes and especially for the majority of patients who require less intensive treatment strategies such as those with controlled type 2 diabetes due to life-style modification, oral agent therapy or simple combination oral agent/basal insulin therapy. An equal number of individuals with impaired glucose tolerance and pre-diabetes would benefit from a non-invasive monitoring method to assess their own glucose several times weekly or monthly to detect disease progression. There are also a significant number of patients for whom there is a need for simple non-invasive monitoring for a determinate period of time including women with gestational diabetes, who may or may not be taking insulin, patients with insulin resistance due to heart failure and individuals undergoing chemotherapy or transplant anti-rejection therapies. Thus, there is a very large unmet need for simple non-invasive system.

Existing invasive glucose sensors are commonly used to measure the blood-glucose level of individuals with diabetes. Just by way of example, such sensing systems may be utilized by drawing blood and directly sensing the concentration of glucose in the blood. The problem with these types of sensors is that they are painfully invasive, time consuming, raise concerns about blood borne pathogens, can be embarrassing, and especially troublesome for children. Continuous glucose monitoring (CGM) systems are also available but they are indwelling, suffer from many of the same issues as finger stick devices, and additionally require frequent calibration.

An improved alternative to these invasive glucose sensors is an optical glucose sensor, which is noninvasive. Optical glucose sensors are capable of quantitatively determining the concentration of optically active substances in the human body. As understood by those skilled in the art, the plane of polarization of linearly polarized light rotates as it interacts with optically active material, such as glucose.

FIG. 1 illustrates the principle by which the concentration of an optically active material can be measured utilizing an optical sensor. Unpolarized monochromatic light 100 is passed through a vertical polarizer 105. The linearly polarized light 110 exiting the vertical polarizer 105 is subsequently passed through an optically active sample 115, such as a sample containing glucose. The optically active sample rotates the plane of polarization of the linearly polarized light 110 by an angle, $\phi$, which is proportional to the concentration of the optically active sample. The light exiting the optically active sample is passed through a horizontal polarizer 120. The intensity of the light passing through the horizontal polarizer 120 and detected by the light detector 125 is related to the horizontal component of the plane of polarization introduced by the rotation of the vertically polarized light by the optically active sample 115. Therefore, for a fixed path length through the sample chamber the intensity of the light measured by the detector 125 is proportional to the concentration of the optically active sample.

The fluid contained in the anterior chamber of the eye is known as the aqueous humor and is relatively scatter free, making the anterior chamber an ideal sampling point to detect glucose concentrations utilizing an optical sensor. The diffusion or secretion of glucose into the aqueous humor is highly correlated to the amount of glucose found in the blood. More specifically, the aqueous humor fluid yields a glucose content equal to approximately 70% of that found in blood. Thus, an individual's blood glucose concentration can be ascertained by an optical glucose sensor that detects changes in the plane of polarization of linearly polarized light directed through the anterior chamber of the individual's eye. Examples of such optical glucose sensors may be found in U.S. Pat. Nos. 6,885,882 and 5,209,231, which are herein incorporated by reference.

BRIEF DESCRIPTION OF THE DRAWINGS

Features and advantages of embodiments of the present invention will become apparent from the appended claims, the following detailed description of one or more example embodiments, and the corresponding figures. Where considered appropriate, reference labels have been repeated among the figures to indicate corresponding or analogous elements.

FIG. 7(A) is a spot diagram using rays in circular pattern 5×5 rays of red and green beams with the total surface area set to 3 mm×3 mm for the detector area size and FIG. 7(B) is a profile showing repeatable beam shape under 3 mm×3 mm which is the current size of the detector surface in an embodiment.

FIGS. 17(A) and 17(B) address how embodiments have different distances between mirrors, which may more easily be coupled to a user's eyeglass frame, headset, and the like.

DETAILED DESCRIPTION

Reference will now be made to the drawings wherein like structures may be provided with like suffix reference designations. In order to show the structures of various embodiments more clearly, the drawings included herein are diagrammatic representations. Thus, the actual appearance of the structures, for example in a photomicrograph, may appear different while still incorporating the claimed structures of the illustrated embodiments. Moreover, the drawings may only show the structures useful to understand the illustrated embodiments. Additional structures known in the art may not have been included to maintain the clarity of the drawings. "An embodiment", "various embodiments" and the like indicate embodiment(s) so described may include particular features, structures, or characteristics, but not every embodiment necessarily includes the particular features, structures, or characteristics. Some embodiments may have some, all, or none of the features described for other embodiments. "First", "second", "third" and the like describe a common object and indicate different instances of like objects are being referred to. Such adjectives do not imply objects so described must be in a given sequence, either temporally, spatially, in ranking, or in any other manner. "Connected" may indicate elements are in direct physical or electrical contact with each other and "coupled" may indicate elements cooperate or interact with each other, but they may or may not be in direct physical or electrical contact.

Figure 1:
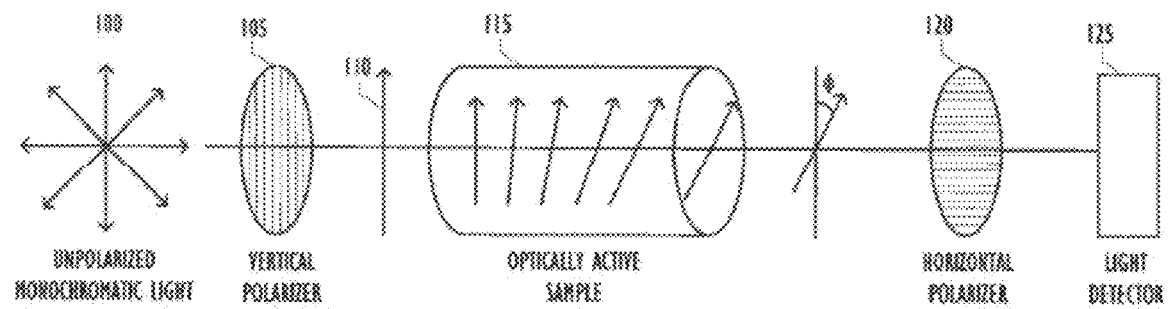
FIG. 1 is a block diagram illustrating a fundamental approach to detect the concentration of an optically active sample based on the rotation of the plane of polarization of linearly polarized light passed through the sample.
Figure 2:
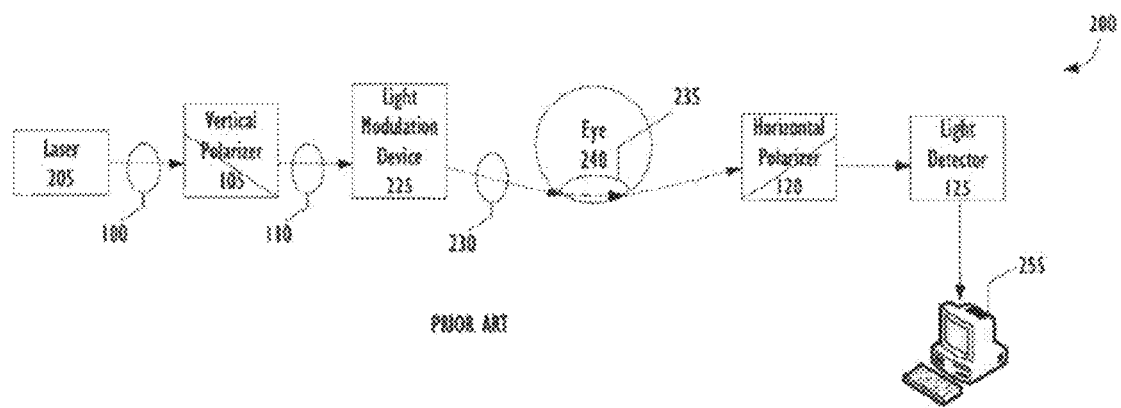
FIG. 2 is a block diagram of an optical glucose sensor utilizing a magneto-optic polarization modulation device.

Although the example process illustrated in FIG. 1 is suitable for measuring large concentrations of optically active substances, Applicant determined additional measures must be taken to accurately measure the relatively small physiological concentration of glucose in the aqueous humor. As illustrated in FIG. 2, a polarization modulation device 225 is added to the example system of FIG. 1 to modulate the plane of polarization of linearly polarized light using the Faraday Effect. According to the Faraday Effect, the plane of polarization of light traveling through a magneto-optic material is rotated by an angle proportional to the magnitude of a magnetic field parallel to the propagation direction of the light, the Verdet constant of the magneto-optic material, and the length of the material according to the formula $\beta=vBL$, where $\beta$ is the magnitude of rotation of the plane of polarization, B is the applied magnetic field, v is the Verdet constant of the magneto-optic material, and L is the length of the magneto-optic material.

The induced modulation allows for the detection of the submillidegree rotational changes, in the plane of polarization, in the presence of optically active substances (e.g., glucose) in the aqueous humor. Due to the relatively short path length and small analyte concentrations present in the aqueous humor, detection of changes in the plane of polarization on the order of 0.4 millidegrees are needed to obtain a system sensitivity comparable to current glucose sensing devices. Utilizing the modulation device, the concentration of glucose can be determined based on the difference between the observed intensity of light at light detector 125 and the expected intensity based on the intentionally induced modulation. Therefore, modulation makes it possible to isolate and detect the small variations in the rotation of the plane of polarization caused by the changes in the concentration of glucose present in the aqueous humor. Detection of the small rotational changes in the optical signal due to the presence of glucose is possible through the use of lock-in amplifiers used to detect the modulated signal. This greatly increases the signal to noise ratio through isolating the modulated signal, thereby, reducing the effects of lower frequency sources of noise such as 60 Hz frequencies emitted by light fixtures in the area of the sampling, thereby improving the sensitivity of the system enabling glucose detection by means of coupling polarized light across the anterior chamber of the eye.

Regarding the lock-in amplifiers and other circuit based components, U.S. Pat. No. 6,885,882 includes numerous descriptions of processing equipment now known to those of ordinary skill in the art. As a result, discussions regarding such circuit based technology are avoided here for clarity and brevity.

Thus, according to the system for optically sensing glucose levels illustrated in FIG. 2, a laser 205 emits light 100 into a vertical polarizer 105. The polarized light 110 then passes through a polarization modulation device 225. The polarization modulation device 225 rotates the plane of polarization at a frequency (f) with a modulation depth of ±β by applying a magnetic field parallel to the direction of propagation of the polarized light 110 through a magneto-optic material. The modulated light 230 then passes through the aqueous humor fluid 235 contained in the anterior chamber of the eye 240, wherein the plane of polarization is further rotated according to the concentration of optically active molecules in the aqueous humor fluid 235, wherein glucose is the primary optically active molecule. The modulated light 230 next passes through a horizontal polarizer 120 in the same manner as described above with respect to FIG. 1. A light detector 125 measures the intensity of the modulated light 230 and converts it into an electrical signal to be analyzed by a processing unit 255, such as a personal computer, in order to determine the concentration of glucose in the aqueous humor.

Figure 13:
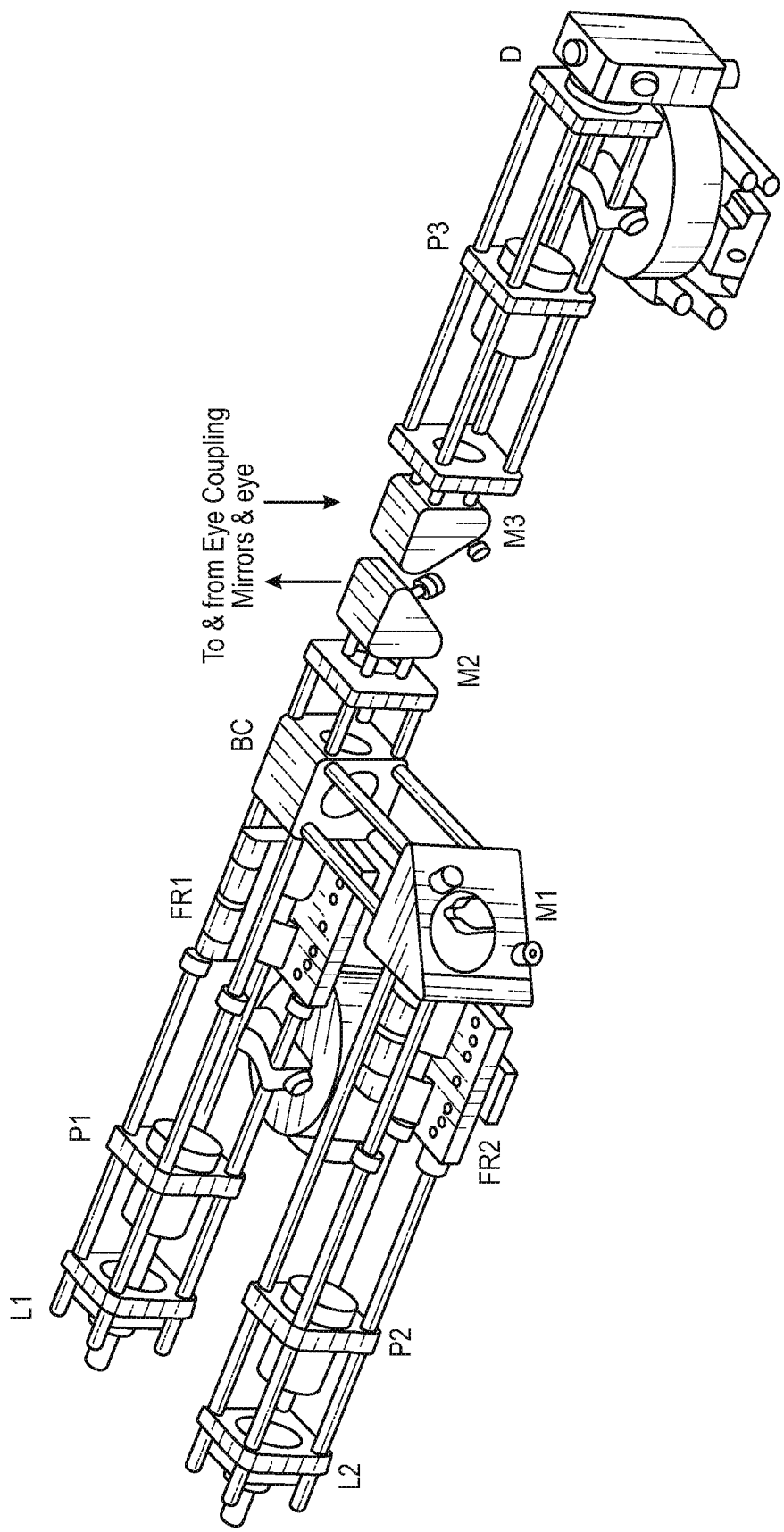
FIG. 13 illustrates an embodiment of a system that includes two lasers heterodyned with the polarization modulators.

One embodiment of the optical setup that uses two wavelengths is illustrated in FIG. 13. Although modulation provides sensitivity in the system, the cornea of the eye produces birefringence. In particular, as the cornea moves it produces time varying birefringence, which is a type of noise that provides a loss of specificity that Applicant determined cannot be compensated using the single wavelength system of FIG. 2. Therefore, an embodiment includes a method of obtaining both the specificity and sensitivity using the dual wavelength dual modulation system of FIG. 13. Fundamentally, the two wavelengths can be combined in a manner that removes the time varying corneal birefringence noise and provides better specificity.

In FIG. 13 the two optical sources used in the design, L1 and L2, are relatively smaller footprint and longer wavelength laser diodes since they offer temperature control, can be used as one mechanism to enhance specificity by overcoming time varying corneal birefringence, and can provide amplitude modulation up to the megahertz range using either current or voltage variation to drive the laser, if a dual modulation approach is desired. The laser diodes are followed by Glan-Thompson linear polarizers, P1 and P2, that provide strong horizontal linearly polarized states. The individual beams pass through the polarization modulation devices, FR1 and FR2, that operate as both modulators and rotational compensators in order to achieve the AC modulation in the hundreds of kilohertz range and DC closed-loop feedback control. After single or dual modulation from the polarization modulating devices and the two lasers, the two beams are overlaid on top of each other using a beam-splitter/combiner, BC. The combined light beams are passed through the adjustable mirror, M2, through the eye at a glancing angle, and directed and collimated by a set of concave mirrors, M3. The beams, after collimation, are coupled through a linear polarizer, P3, which is positioned perpendicularly to the initial polarizers to act as an analyzer to the optical beams. The beams are coupled to the detector, D, and converted into electronic signals using a photodiode.

While these optical glucose sensors (FIGS. 1 and 2) are an improvement over invasive glucose sensors, Applicant determined that problems remain. For example, to accurately measure glucose concentrations in the aqueous humor, optical glucose sensors require accurate coupling of polarized light across the aqueous humor. The aqueous humor is the area between the lens and the cornea. The light cannot be simply directed toward the lens and reflected back out of the eye since this would potentially allow too much light to impinge directly on the retina beyond safety standards. In addition, the lens flips the rotation of the polarization vector by 180 degrees and hence the net rotation of the polarization vector of the light due to the glucose would be zero thereby not allowing for the glucose concentration to be measured. Existing optical glucose sensors do not describe how to accurately couple the light across the eye and overcome the index of refraction mismatch, while also allowing for overall non-zero measurement of the rotation of the polarization vector of the light due to glucose that would occur, for instance, by simply reflecting the beam from the lens. As noted herein, reflecting light with a lens results in a 180 degree flip in the polarization (so the light polarization rotation from glucose then simple "unwinds" as it comes back out if reflected).

Applicant has therefore pursued a solution to overcome the difficulties Applicant had determined are associated with coupling the light into and out of the eye with current polarimetry based optical glucose sensors. Embodiments of the solution provide a way that light passes across the eye and not to the back of the eye to reach the retina. An embodiment includes a mechanism that does not make physical contact with the eye by using the appropriate mirrors and light angles. Another embodiment uses a coupling scleral or contact lens that makes contact with the eye tissue but in a minimally invasive method as possible.

An embodiment includes an approach to coupling two or more wavelengths of polarized light across the aqueous humor of the eye. Some embodiments include non-contact mirrors while other embodiments include a contact method that uses a scleral or corneal lens for minimal contact coupling. In various embodiments, the non-contact coupling takes the form of a desktop device with features similar to the common slit lamp, a hand held device similar to a hand-held ophthalmoscope, or ultimately in the form of intelligent eye ware similar to virtual goggles or glasses. An embodiment includes a minimal contact method that uses an index matching wearable such as a sclera lens or contact lens. Various contact and non-contact embodiments include sensors for macro level adjustment that find the peak signal and/or a manual fine tuning adjustment mechanism that improves the signal quality and automates the beam coupling optimization prior to making a non-invasive glucose measurement. The macro and fine tuning adjustments are important since each patient will have a slightly different anatomical eye protrusion and thus will need an individually tailored adjustment but one that is simple for the patient or physician to make the measurement. The coupling mechanism described is a critical design area in allowing for a polarimetric sensing device, attempting to pass two or more wavelengths of polarized light through the eye, to evaluate glucose levels in subjects without the need to draw blood for each measurement.

Figure 3:
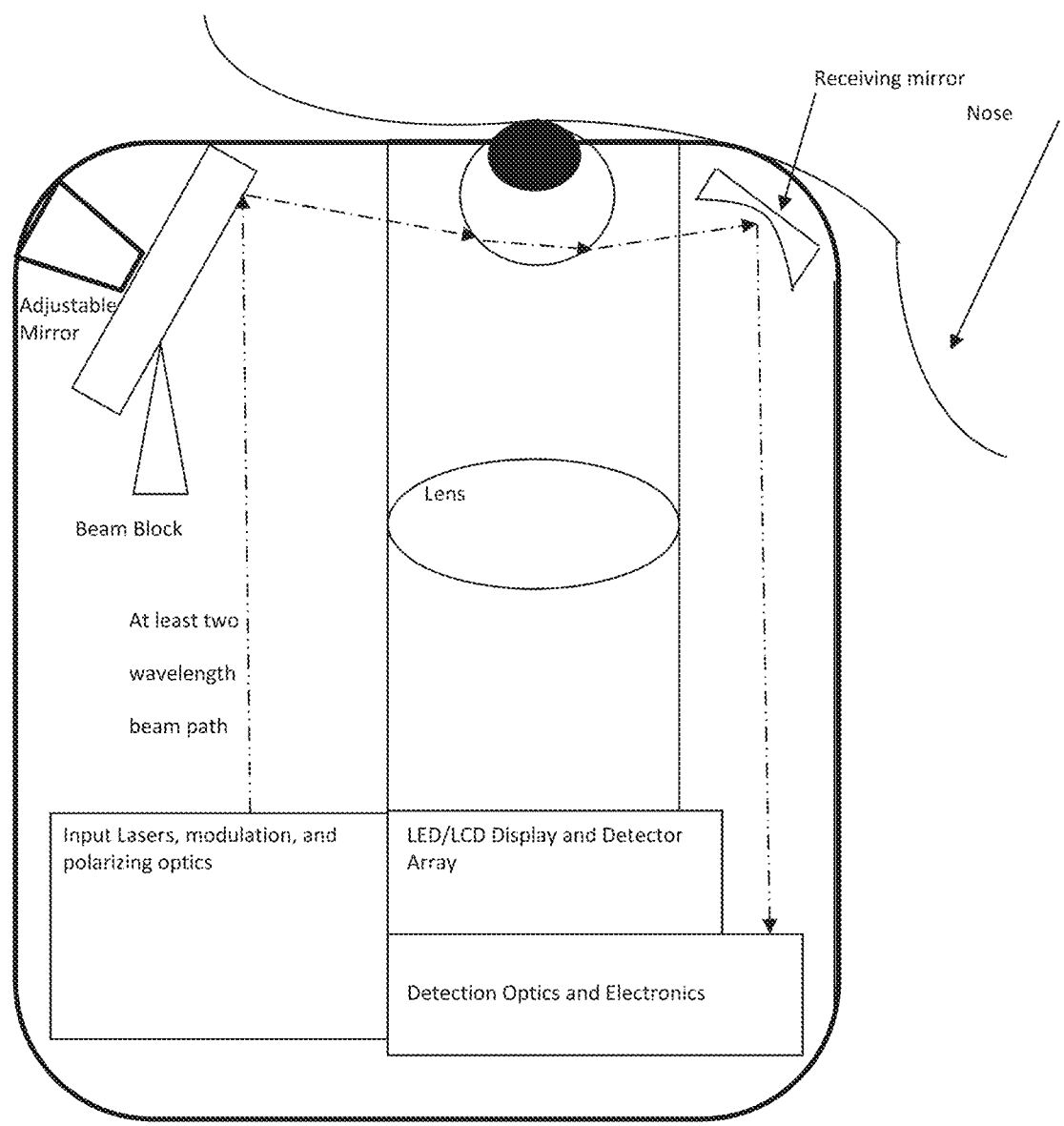
FIG. 3 is a schematic of one embodiment that resembles a hand-held ophthalmoscope showing the beam coming from the input laser and optics, reflecting off an adjustable flat mirror across the aqueous humor of the eye, off a second mirror, and back into the unit's detection optics and electronics. The unit also shows a detector array for providing feedback to the adjustable mirror(s) and an LED/LCD display allowing the patient to focus thereby minimizing the gross motion artifact.

Referring to FIG. 3, one embodiment is a device approximately the same size and that takes on the appearance of a handheld ophthalmoscope. Some elements of operation of the device are described in detail with regard to FIG. 2 and FIG. 13. A principle of operation begins with two or more wavelengths of light with polarized beams that are sent off of a mirror, adjustable for alignment, with a built in stop to ensure that no incident light reaches the retina. The adjust could be a manual screw adjustment to align the beam correctly through the aqueous humor at a glancing angle or an automated adjustment which is electro-mechanically controlled (i.e. piezo) and receives feedback from the light collected from the detector array. The polarization vector of the beams is then rotated in an amount proportional to the glucose concentration as they pass through the aqueous humor of the eye. The beams are then collected with a concave mirror for recollimation and sent through the detection optics. The concave mirror could also be manually or automatically (i.e., with piezo system) adjusted as needed. The rotation is seen as a change in intensity on the detector and converted by the electronics to a liquid crystal display (LCD) reading of the glucose for the user, which can also simultaneously be stored (e.g., in at least one memory, such as a memory in a smartphone, which is wirelessly coupled to the system). The detector array and LED/LCD panel has been added to not only be used for displaying the reading but for feedback to the automated adjustable mirror and for alignment and calculation of the path length by insuring the patient focuses their eye to the same point each time. Instead of an LCD array, an optical target such as a lighted cross hairs could be used for aligning the eye in the proper direction for coupling.

Figure 4:
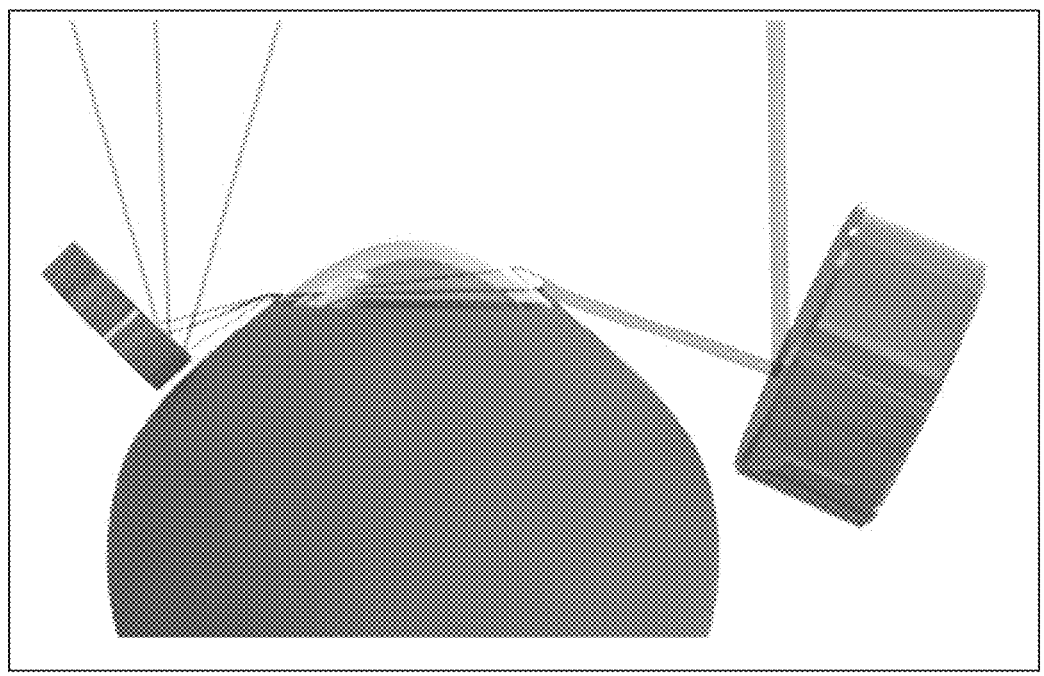
FIG. 4 is a model of one embodiment of the optical path around the eye for two wavelengths of light through the anterior chamber of the eye for unmatched refractive indices using a flat round mirror on each side. Note that reflective optics such as mirrors rather than transmissive optics such as lenses also have the added advantage of minimizing aberrations, particularly when using two or more wavelengths.
Figure 5:
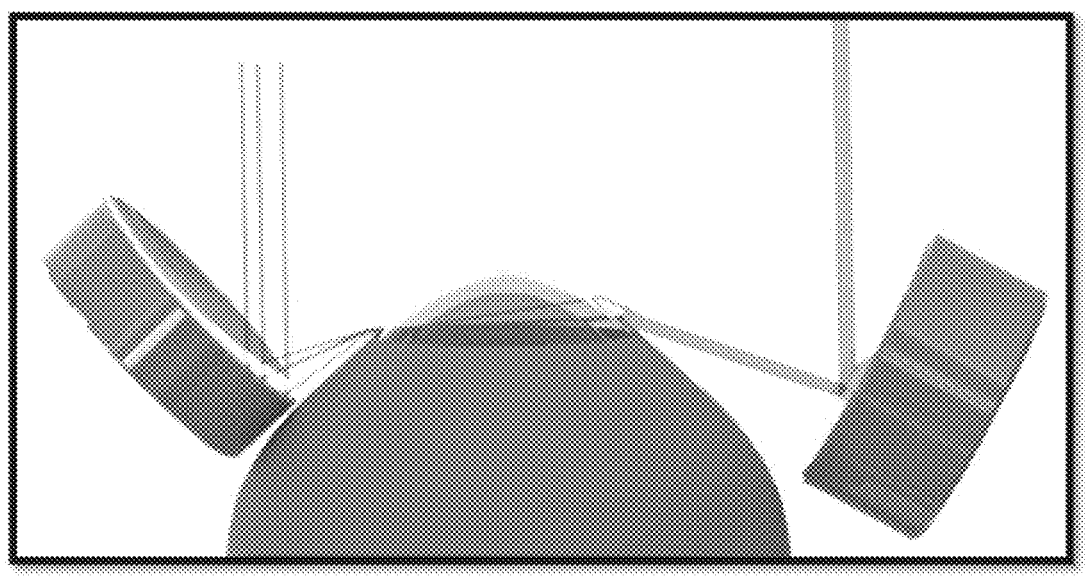
FIG. 5 is a model of one embodiment of an improved optical path for two wavelengths of light through the anterior chamber of the eye for unmatched refractive indices using a flat round mirror on the entrance side and a concave mirror on the collection side showing the advantage of the concave mirror for collimating the light.

Referring to FIG. 4 and FIG. 5, depicted is a detailed modeling of the path lengths of the light from the input mirror through the eye to the output mirror using two wavelengths of light for non-contact eye coupling devices. Note that according to the modeling of the optical path through the anterior chamber of the eye for unmatched refractive indices, there is no visible difference between the optical paths taken through the eye by the two beams at different wavelengths, and hence, a single beam path is shown. The two designs use reflective optics (such as, but not limited to, mirrors) rather than transmissive optics (such as lenses) in order to provide the advantage of minimizing aberrations, particularly when using two or more wavelengths. However, FIG. 4 also shows the output beam is not collimated due to the index of refraction mismatch and hence may include coupling optics after the output for re-collimating. However, the embodiment of FIG. 5 places a 90° concave mirror on the output to re-collimate the formed beam exiting the eye. This mirrored configuration is not meant to be limiting. As aberration optics become better and more cost effective it is envisioned that some or all of the mirrors described herein may be replaced with such transmissive optics.

The use of the concave mirror in FIG. 5 allows for gathering all or most of the light dispersed as it leaves the eye. Furthermore, using mirrors, in general, as noted in embodiments described herein allows for multiple wavelengths to be collimated after coming from the eye as opposed to lenses which, if used, could cause aberrations or bending of the different wavelengths at different angles, which would not allow effective light collimation coming from the non-index matched eye.

Figure 6:
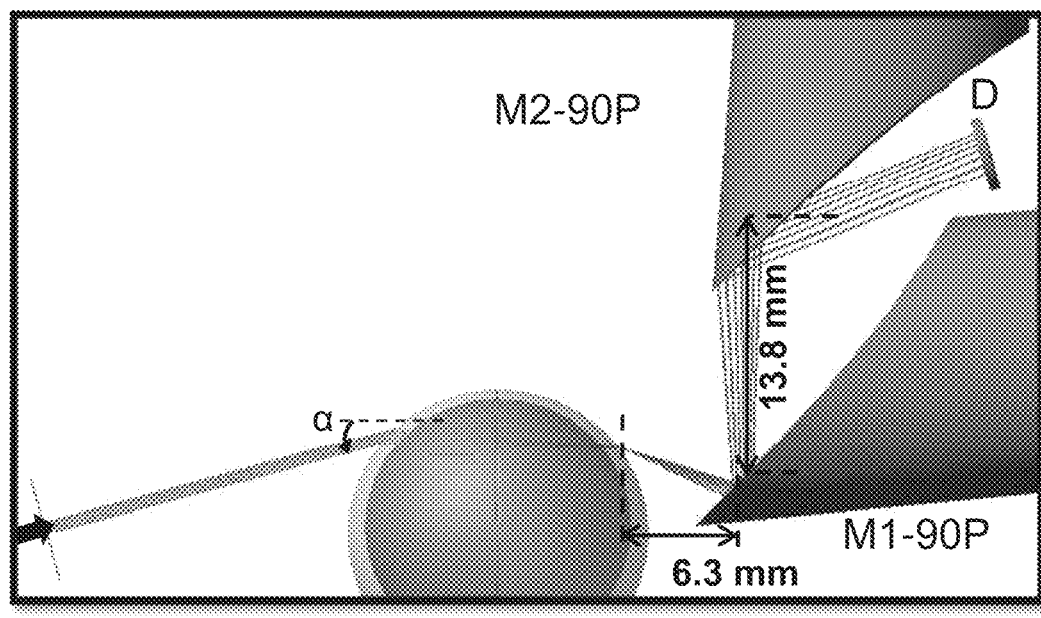
FIG. 6 is a CODE V simulation of one embodiment of an improved optical path for two wavelengths of light through the anterior chamber of the eye for unmatched refractive indices utilizing two 90 degree off-axis parabolic mirrors for re-collimating the beam exiting the cornea in addition to a flat round mirror guiding the entrance beam into the cornea at a specified glancing angle with solid fill.

FIG. 6 depicts an embodiment of proposed non-index matched eye-coupling scheme utilizing two 90 degree off-axis parabolic mirrors to more precisely re-collimate the beam exiting the cornea in addition to a round mirror guiding the entrance beam into the cornea at a specified glancing angle as simulated using CODE V. Utilizing the CODE V optical modeling software, the angle of incidence for each configuration as measured from the horizontal has to be at a relative glancing angle with respect to the posterior corneal surface in order for the beam to exit the anterior chamber through the cornea in both configurations and since each person has a slightly different corneal protrusion this input mirror may need to have an adjustment that would need to be performed as a one-time calibration. The glancing angle ($\alpha$) for the entrance beam using an average anatomical eye of 16 degrees was determined optimal but this could vary depending on each individual and is the reason an adjustable mirror is required at the input to the eye. Other embodiments include glancing angles of 5, 10, 15, 20 degrees or more. Evaluating the beam position of the two wavelengths at the detector and the appearance of the two beam ray traces the x, y, and z position of the two 90 degree off-axis parabolic mirrors was varied until optimal results were obtained maximizing the overlap between the wavelengths and minimizing the change in the optical signal observed on the detector over multiple simulations. The parameters specified by THORLABS were utilized in designing the mirrors in CODE V but other mirrors could be used. After the optimal position was determined for each element a CAD rendering of the ray trace starting with the entrance beam up to the beams onto the detection optics were output in STL format. Then utilizing SolidWorks a 3D model was generated of the respective ray traces for the individual wavelengths with the exported file as a reference. Using the CODE V output ray traces and CAD models for the optical elements, a human eye, and a rendering of a human face obtained via scanning a face into a 3D representation it was possible to evaluate the placement of the optical elements and beam path as shown by the models in FIG. 6. Thus, the eye was modeled in the various software packages and the ray trace for 635 nm and 532 nm wavelengths of the respective models are shown in FIG. 6 but could vary across the visible to near infrared wavelength range. For each optical model, the beam diameter was chosen to be circular with a diameter of approximately 1 mm but could be from 0.5 mm to 3 mm and still couple through the eye depending on the individual person's eye.

Figure 7:
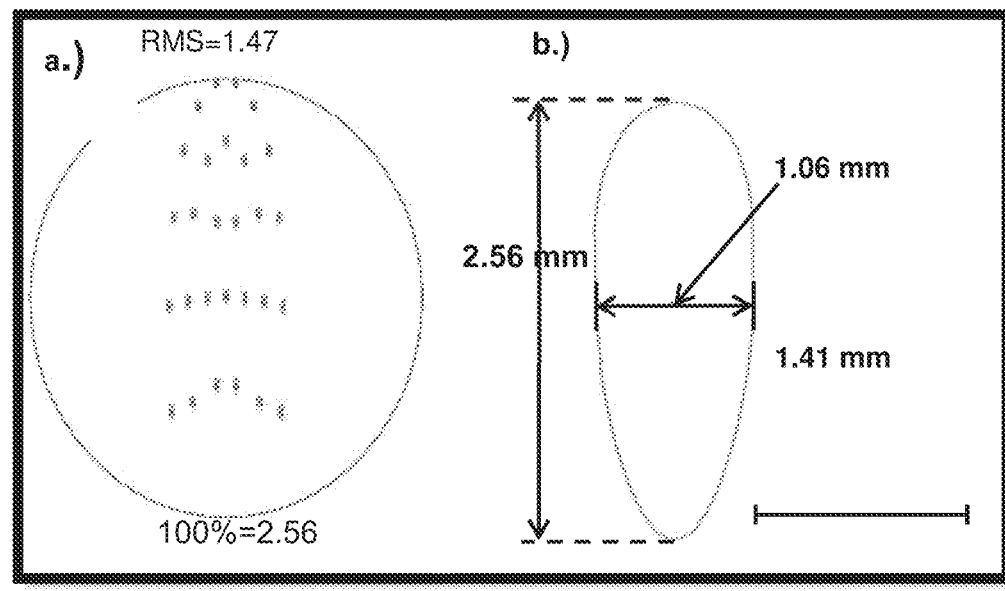
FIG. 7 is a CODE V simulation spot ray trace simulation output at the detector for the model shown in FIG. 6. Specifically.

FIG. 7 depicts the CODE V simulation of the beam profile at the detector for the optimized model shown in FIG. 6 assuming a 1 mm circular beam input. Multiple simulation runs were conducted and minimal change in the profile was observed.

Figure 8:
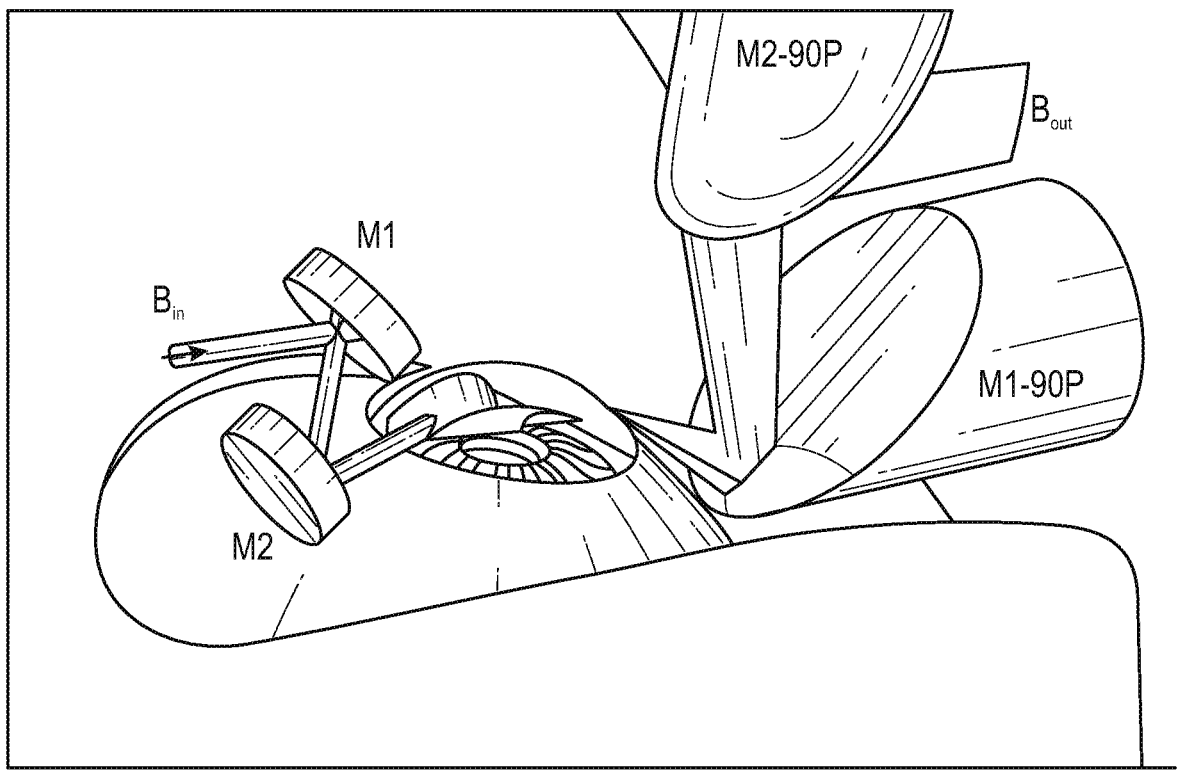
FIG. 8 is a Zemax simulation of the embodiment for the proposed non-index matched eye-coupling scheme utilizing two round mirrors guiding the entrance beam into the cornea at a specified glancing angle and two 90 degree off-axis parabolic mirrors re-collimating the beam exiting the cornea in addition

FIG. 8 depicts a Zemax simulation of proposed non-index matched eye-coupling scheme showing more of the anatomy of the eye and face for the embodiment utilizing two 90 degree off-axis parabolic mirrors to re-collimate the beam exiting the cornea in addition to two round mirrors guiding the entrance beam into the cornea at a specified glancing angle.

Figure 9A:
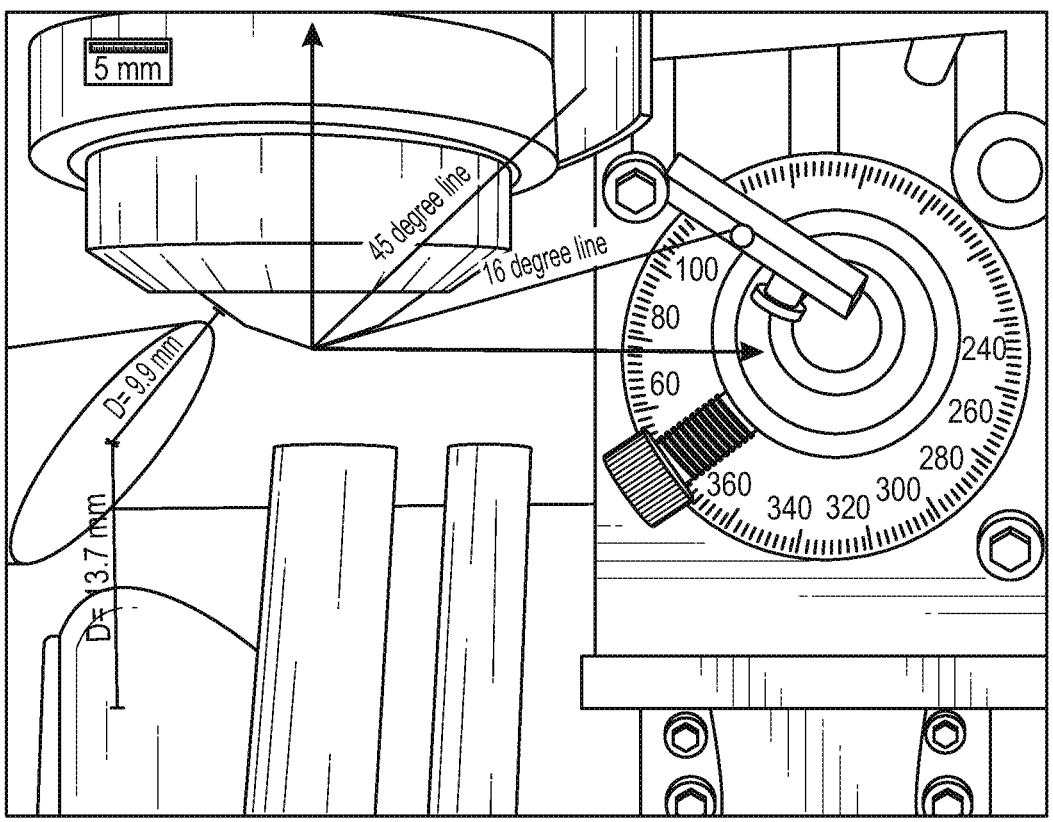
FIG. 9A is an experimental setup showing the flat mirror coupling (right side) at a 16 degree angle from horizontal coupling the light through a human cornea mounted at the correct pressure on a blue mount and the off axis 90 degree mirror on the left side collecting the light.

An experimental setup was FIG. 9A

Figure 9B:
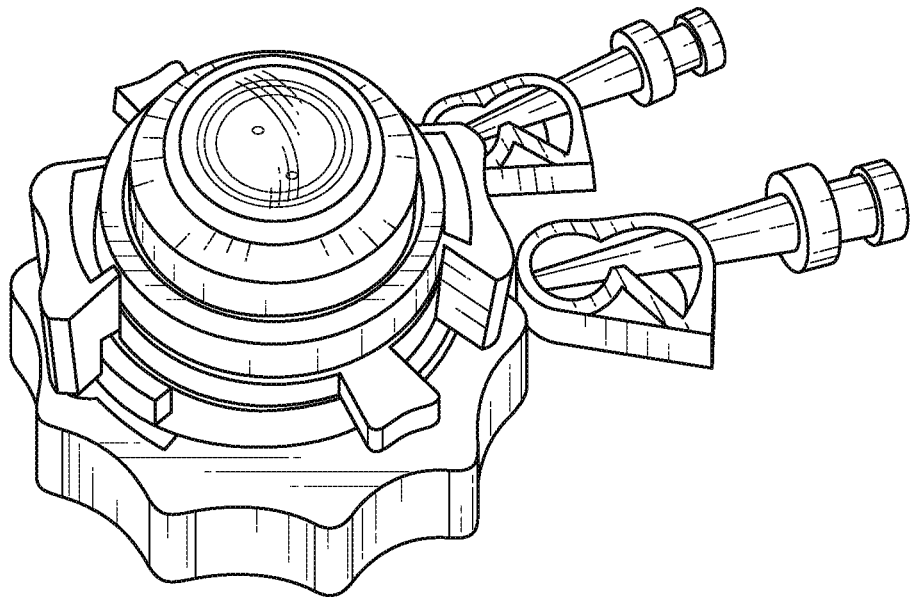
FIG. 9B is a close up view of the in vitro human eye cornea holder and tubes for pressurizing the device at the correct ocular pressure.
Figure 10A:
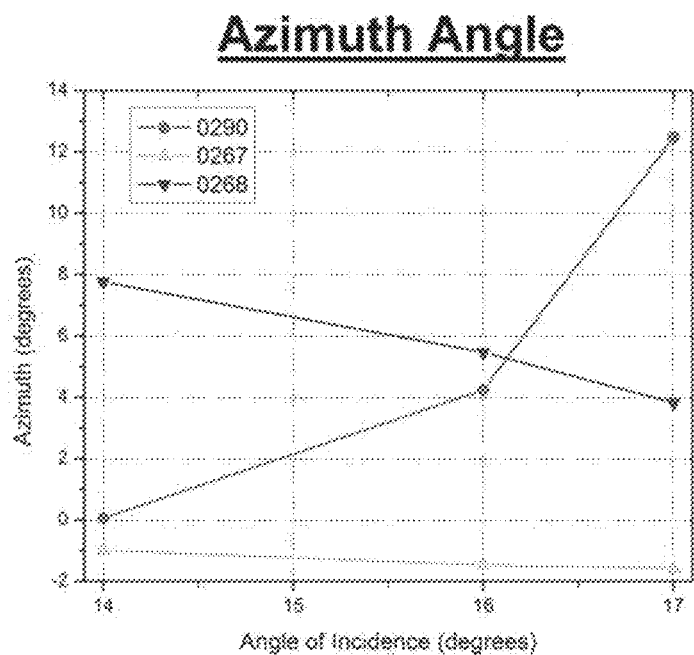
FIG. 10A is the azimuth angle measured across three different human corneas mounted for three angles of incidence using the setup depicted in FIG. 9.
Figure 10B:
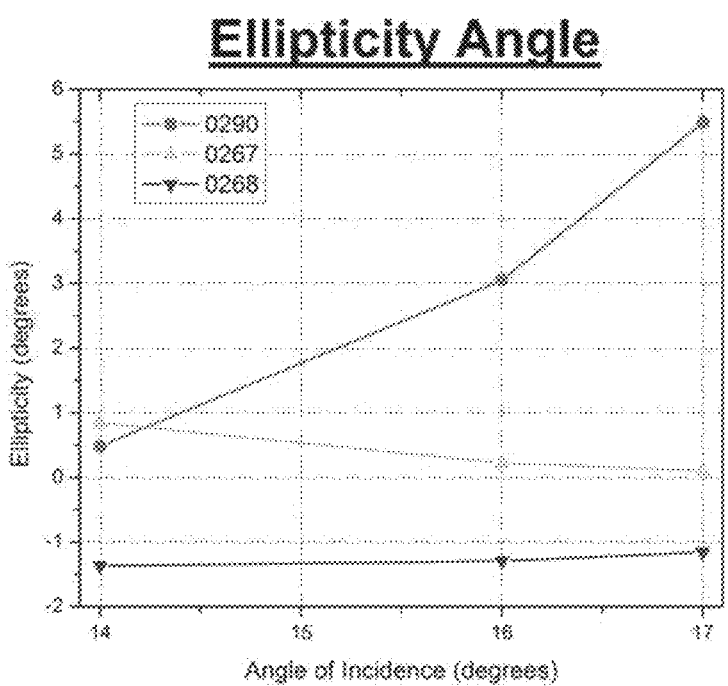
FIG. 10B is the resultant ellipticity measurement using the setup depicted in FIG. 9
Figure 10C:
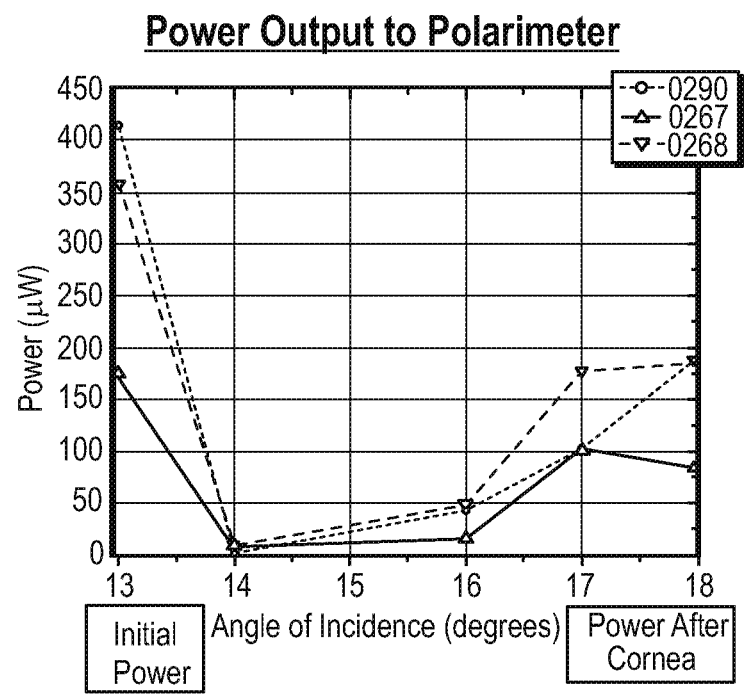
FIG. 10C is the power output measured at the end of the optical train using the setup depicted in FIG. 9.

Using the model depicted in FIG. 6 an experimental optical system was developed to assess the light coupling through a human cornea as shown in FIG. 9A. The system included a human cornea housing chamber as shown in FIG. 9B that provided control for both the pressure imposed on the human cornea and fluid bathing the cornea. Using this system, cornea's from three human subjects were mounted onto the eye mount chamber shown in FIG. 9B and polarization measurements were acquired with a Thorlabs polarimeter prior to and after the coupling through the eye. Using the acquired measurements, the azimuth (FIG. 10A), ellipticity (FIG. 10B), and power (FIG. 10C) measurements were examined at three varying angles (14 degrees, 16 degrees, and 17 degrees) with respect to the optical axis. For these tests, a 632 nm laser diode was used with a laser spot size of approximately 2 mm. The power before the eye was set to around 420 microwatts and the cornea pressure was fixed at 16 mmHg with the anterior glucose solution consisting of a 100 mg/dL solution of glucose. As depicted the angle of incidence does affect all three measurements and hence the input mirror may need to be adjustable in order to optimize the output signal per patient.

Figure 11:
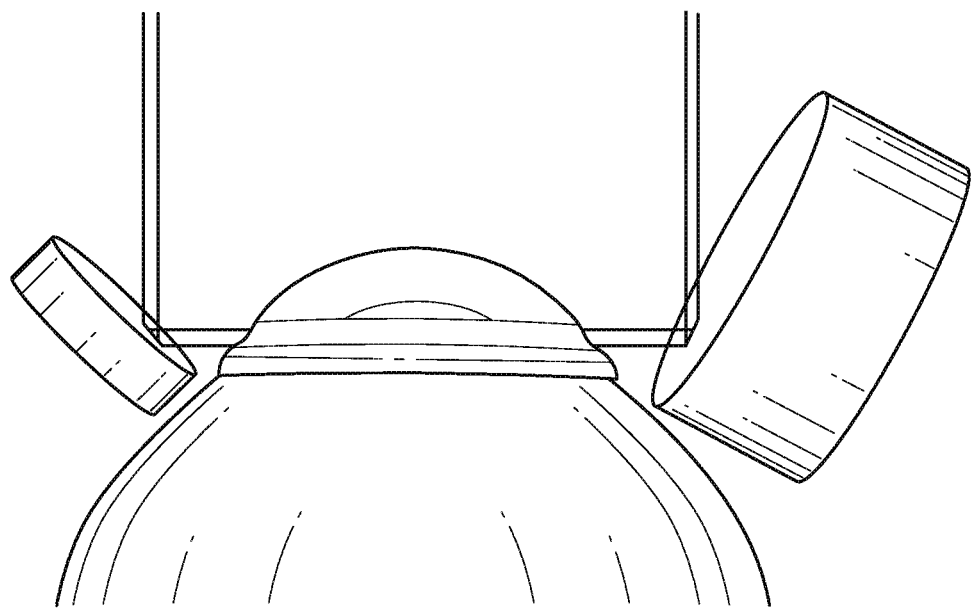
FIG. 11 is a model of the light beams across the eye using a minimal contact scleral or corneal contact lens type of coupling device. In this case two round flat mirrors at 45 degrees can be used for guiding the input and output light with no dispersion since the index of refraction is matched.

FIG. 11 depicts a minimal contact embodiment. The approach uses an index matching sclera or corneal contact lens. The approach, although still noninvasive, may require an index matching contact or scleral lens to be inserted. In an embodiment the lens does not cover the cornea but rather is a doughnut shaped lens inserted at the cornea/sclera interface. This lens is similar to current contact lenses used frequently today in terms of pliability and ability to be inserted but, due to its doughnut shape does not affect the vision. Although the lens may not be a perfect match to the cornea, which has an index of 1.376, our CAD modeling depicted in FIG. 11 indicates that they would be enough to allow translation across the anterior chamber without the need for a glancing angle.

Figure 12A:
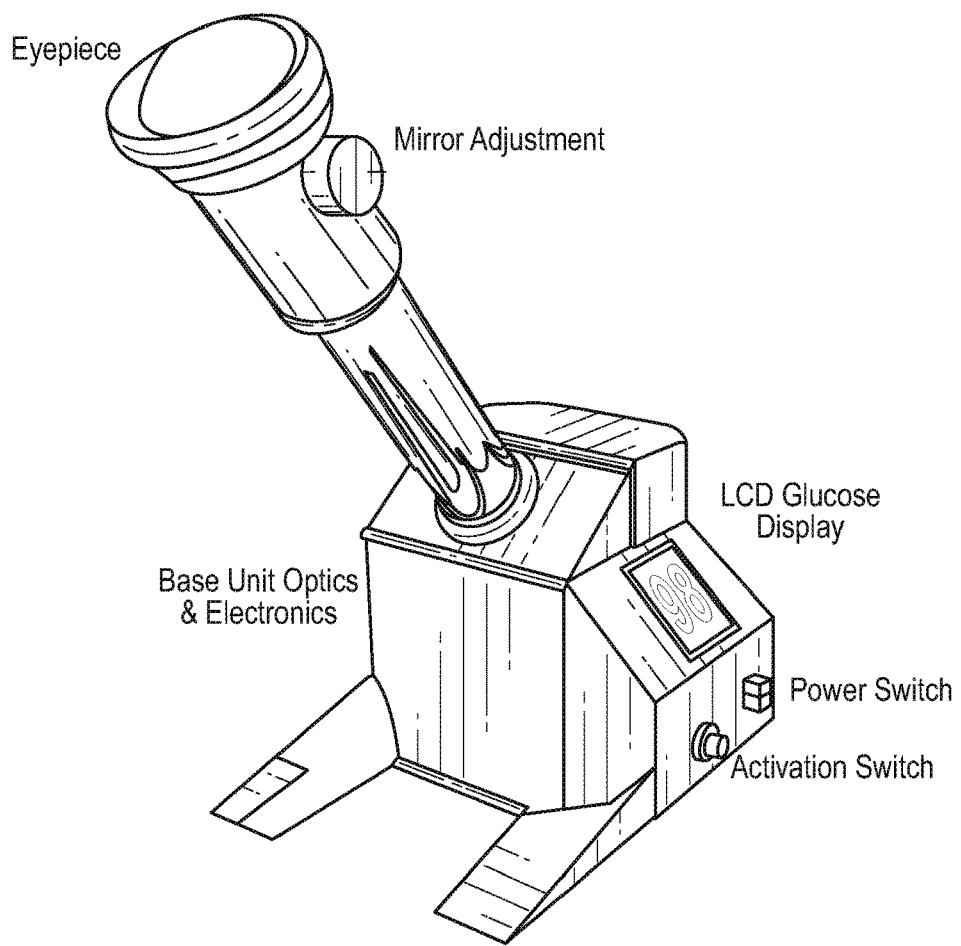
FIG. 12 shows pictures or drawings of two different embodiments from that of FIG. 3 including FIG. 12(A) a bench-top coupling system and FIG. 12(B) Intelligent eye ware coupling system.
Figure 12B:
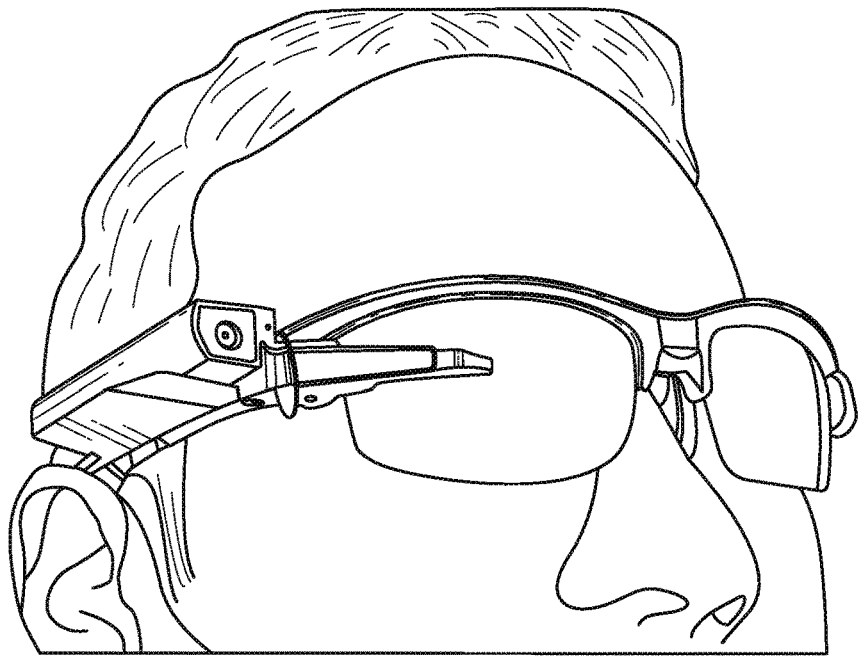

FIG. 12A and FIG. 12B show pictures of two different embodiments from that of FIG. 3 including a bench-top coupling system and intelligent eye ware coupling system. The system components are comparable to those of FIG. 2 and FIG. 3 but the form factor allows for either more stability and less degrees of freedom in terms of motion for the table top system shown in FIG. 12A or more convenience and real time monitoring as depicted in the intelligent eye ware of FIG. 12B.

As illustrated in the example embodiments described above, various properties of the improved eye coupling device can be selected to optimize the coupling. For example, the mirror size to minimize interference from eye lashes, the mirror angle adjustment (manual or automated) and radius of curvature for the collecting mirror. In addition, the mirrored surfaces used for the modeling were silver coated but could be gold or other reflective material that allows for multiple wavelengths across the visible and near infrared spectrum. Accordingly, the desired form factor for the improved polarization eye coupling device for a particular individual eye anatomy will dictate the specific design of the device.

It is to be understood that the present invention is not limited to the above embodiments. For example, the silver coated, concave and off-axis parabolic mirrors used in FIGS. 5 and 6 are described only to illustrate one embodiment of an eye coupling device and is not intended to be limiting in any manner. The coupling angles and mirror types can be adjusted to be on axis or off axis to function to both gather all of the light coming out of the eye and collimating that light back into the detection optics and detector. In addition, the depicted design of the polarized light eye coupling device in FIG. 3 is not intended to be limiting in any manner. Rather, the light eye coupling device includes any coupling device form factor that can couple polarized light across the aqueous humor of the eye.

Thus, as shown herein some embodiments of the invention relate generally to improved methods, systems, and apparatuses for coupling polarized light at two or more wavelengths across the aqueous humor of the eye for multiple uses (e.g., as part of a noninvasive glucose monitoring system). An approach discloses non-contact and minimal contact eye-coupling designs that are part of a system for providing glucose concentration levels via measurements acquired by passing two or more optical beams through the cornea/aqueous chamber in the eye. The approach provides for coupling the light to account for the index mismatch (mismatch between indexes of refraction for air and eye tissue) incurred while allowing for monitoring the light polarization. Specifically, in an embodiment the light transitions from the device, through the air, through the proximal side of the cornea, through the aqueous humor, through the medial side of the cornea, and through the air back into the device. Embodiments described herein address the index of refraction mismatch and polarized light maintaining concerns with a coupling approach (where mirrors are used to couple light beams to the eye and from the eye) that can take the form of contact and non-contact mechanisms. The specific arrangement of mirrors helps ensure the light beams are not directed into the eye (e.g., towards the retina) but instead across the eye (e.g., across the aqueous humor). Embodiments are integrated into various forms such as a desktop device with a monocular that is similar in size to a slit lamp, a hand held device similar to an ophthalmoscope, devices similar to virtual reality goggles, and as glasses (eye ware).

As used herein, "collimate" means that light does not diverge or converge but travels in a cylindrical beam shape (i.e., parallel).

As used herein, "couple" means being able to transmit effectively from one medium to another (i.e., from air to cornea and cornea back to air). Numerous embodiments described herein co-locate multiple beams (i.e., couple two wavelengths from air to the cornea in a way that the two wavelengths are co-located or rather roughly follow the same path). This is important to ensure each travels the same distance through a medium (e.g., tissue, such as aqueous humor).

While conventional technologies (and basic anatomy) couple light into the eye such that it hits the back of the retina, embodiments described herein instead couple light such that the light travels a path across the eye (instead into the back of the retina). This is challenging without a coupling media (i.e., index matching fluid in a tube with the light perpendicular to the tube so it goes straight through the fluid in a collimated way). Thus, one of several points of novelty of numerous embodiments described herein includes the ability to optimally couple the light through the eye without having to index match the eye.

Thus, an embodiment provides advantages over conventional technologies because it couples multiple wavelengths of light across the eye (i.e., into and out of the eye) without the need for adding an index matched medium in between. This is non-trivial and relies on, for example, critical angles (e.g., see FIGS. 4, 5, 6, 7, 8, 9A, 10A, and 10B) determined via extensive modeling as well as experimentation to come up with the correct angles and optics that not only provide the coupling but work around the human anatomy including the bridge of the nose, face, eye socket, and eye-lashes as well as accommodating slightly different eye shapes.

To develop the modeling of unmatched coupling of light across the eye Applicants first needed to use an optical modeling package known as Code V, along with CAD renderings, to evaluate the various coupling schemes and optical component variations as depicted in FIGS. 4, 5, and 6. In these models the ray traces of the beams (at two wavelengths and in three dimensions (x, y, and z)) were calculated with varying positions of the flat and parabolic mirrors until optimal results (including maximizing the overlap between the two wavelengths and minimizing the change in the optical signal) were observed on the detector over multiple simulations for coupling through the eye. For the modeling an optical beam diameter of 1 mm was chosen and, using Code V, Applicants were able to perform polarization ray tracing and solved for the path/surface interactions through the optical system for each wavelength yielding the detector beam profile for both as depicted in FIG. 7. Along with Code V, another modeling program known as Zemax was utilized to evaluate the non-polarized ray trace in the design. In order to perform an anatomical constraint analysis, after the optimal position was determined for each element, a CAD rendering of the ray trace starting with the entrance beam to the detection optics were then output in STL format. This format was then used with SolidWorks to generate a three dimensional model of the respective ay traces for individual wavelengths. Furthermore, by using CAD to develop a three dimensional rendering of the human eye and human face along with the Code V models described, it was possible to evaluate the placement of the optical elements and beam path as shown in FIG. 8. Using the exported models specified in CODE V the model was then evaluated with respect to anatomical features on the human face such as the nose and corneal/sclera surface to determine that the optical model would indeed produce a beam path that was feasible with anatomical constraints. Using the above modeling as a guide, the system of FIG. 9(A) was constructed and the measurements of azimuth angle and ellipticity angle were measured across the aqueous humor of an in vitro human eye at three different angles (14, 16, and 17 degrees) with respect to the optical axis showing that the angle of incidence does affect both measurements. The azimuth angle is the rotation of the orthogonal projection on the reference plane and the ellipticity is the deviation from circularity. The measurements guided by the modeling show that the input mirror may need to be adjustable in order to optimize the output signal polarization angles.

See, for example, example 19a.

For example, the technology of FIG. 1 do not address any optics for coupling in and out of the eye. Also, other conventional technologies show flat mirrors used to couple in and out of the eye but those rely on a reflection from the iris (not actual coupling across the eye while avoiding (to a major degree) the retina). Further, such conventional technologies may not account for coupling difficulties brought on in the "real world" such as, but not limited to, coupling light across the eye of a person that has a nose, eye socket, eye lashes, irregular eye anatomy, and the like.

See, for example, example 19a.

Embodiments also include a scleral lens to perform (at least aid) index matching if coupling without an index matched medium is difficult for a particular patient due to, for example, a unique eye anatomy.

Figure 14:
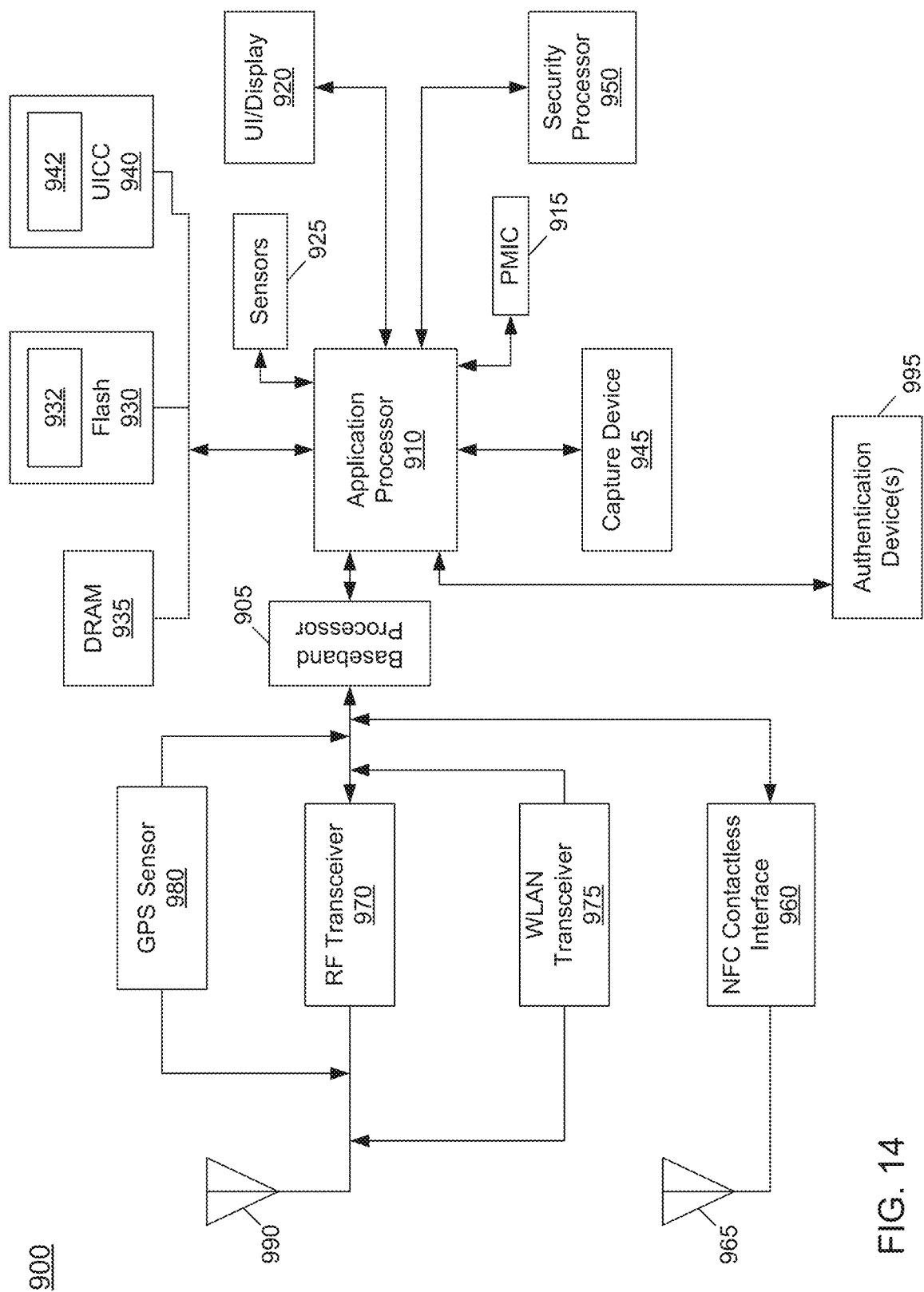
FIGS. 14, 15, 16 include processing systems used in various embodiments.

Referring now to FIG. 14, shown is a block diagram of an example system with which embodiments can be used. As seen, system 900 may be a smartphone or other wireless communicator or any other Internet of Things (IoT) device. A baseband processor 905 is configured to perform various signal processing with regard to communication signals to be transmitted from or received by the system. In turn, baseband processor 905 is coupled to an application processor 910, which may be a main CPU of the system to execute an OS and other system software, in addition to user applications such as many well-known social media and multimedia apps. Application processor 910 may further be configured to perform a variety of other computing operations for the device.

In turn, application processor 910 can couple to a user interface/display 920 (e.g., touch screen display). In addition, application processor 910 may couple to a memory system including a non-volatile memory, namely a flash memory 930 and a system memory, namely a DRAM 935. In some embodiments, flash memory 930 may include a secure portion 932 in which secrets and other sensitive information may be stored. As further seen, application processor 910 also couples to a capture device 945 such as one or more image capture devices that can record video and/or still images.

A universal integrated circuit card (UICC) 940 comprises a subscriber identity module, which in some embodiments includes a secure storage 942 to store secure user information. System 900 may further include a security processor 950 (e.g., Trusted Platform Module (TPM)) that may couple to application processor 910. A plurality of sensors 925, including one or more multi-axis accelerometers may couple to application processor 910 to enable input of a variety of sensed information such as motion and other environmental information.

As further illustrated, a near field communication (NFC) contactless interface 960 is provided that communicates in a NFC near field via an NFC antenna 965. While separate antennae are shown, understand that in some implementations one antenna or a different set of antennae may be provided to enable various wireless functionalities.

A power management integrated circuit (PMIC) 915 couples to application processor 910 to perform platform level power management. To this end, PMIC 915 may issue power management requests to application processor 910 to enter certain low power states as desired. Furthermore, based on platform constraints, PMIC 915 may also control the power level of other components of system 900.

To enable communications to be transmitted and received such as in one or more IoT networks, various circuitries may be coupled between baseband processor 905 and an antenna 990. Specifically, a radio frequency (RF) transceiver 970 and a wireless local area network (WLAN) transceiver 975 may be present. In general, RF transceiver 970 may be used to receive and transmit wireless data and calls according to a given wireless communication protocol such as 3G or 4G wireless communication protocol such as in accordance with a code division multiple access (CDMA), global system for mobile communication (GSM), long term evolution (LTE) or other protocol. In addition a GPS sensor 980 may be present, with location information being provided to security processor 950 for use as described herein when context information is to be used in a pairing process. Other wireless communications such as receipt or transmission of radio signals (e.g., AM/FM) and other signals may also be provided. In addition, via WLAN transceiver 975, local wireless communications, such as according to a Bluetooth™ or WEE 802.11 standard can also be realized.

Figure 15:
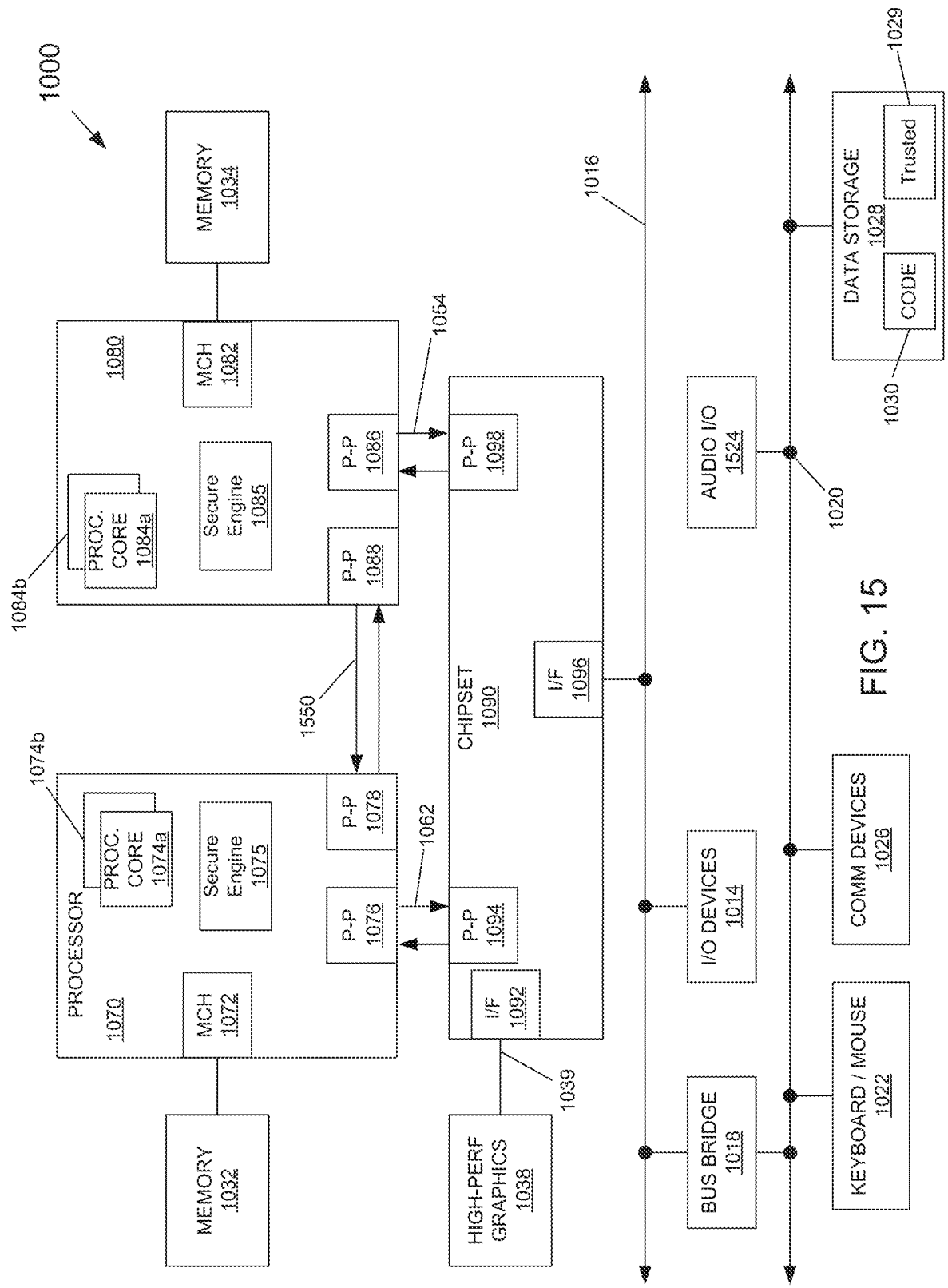

Referring now to FIG. 15, shown is a block diagram of a system in accordance with another embodiment of the present invention. Multiprocessor system 1000 is a point-to-point interconnect system such as a server system, and includes a first processor 1070 and a second processor 1080 coupled via a point-to-point interconnect 1050. Each of processors 1070 and 1080 may be multicore processors such as SoCs, including first and second processor cores (i.e., processor cores 1074a and 1074b and processor cores 1084a and 1084b), although potentially many more cores may be present in the processors. In addition, processors 1070 and 1080 each may include a secure engine 1075 and 1085 to perform security operations such as attestations, IOT network onboarding or so forth.

First processor 1070 further includes a memory controller hub (MCH) 1072 and point-to-point (P-P) interfaces 1076 and 1078. Similarly, second processor 1080 includes a MCH 1082 and interfaces 1086 and 1088. MCH's 1072 and 1082 couple the processors to respective memories, namely a memory 1032 and a memory 1034, which may be portions of main memory (e.g., a DRAM) locally attached to the respective processors. First processor 1070 and second processor 1080 may be coupled to a chipset 1090 via P-P interconnects 1052 and 1054, respectively. Chipset 1090 includes P-P interfaces 1094 and 1098.

Furthermore, chipset 1090 includes an interface 1092 to couple chipset 1090 with a high performance graphics engine 1038, by a P-P interconnect 1039. In turn, chipset 1090 may be coupled to a first bus 1016 via an interface 1096. Various input/output (I/O) devices 1014 may be coupled to first bus 1016, along with a bus bridge 1018 which couples first bus 1016 to a second bus 1020. Various devices may be coupled to second bus 1020 including, for example, a keyboard/mouse 1022, communication devices 1026 and a data storage unit 1028 such as a non-volatile storage or other mass storage device. As seen, data storage unit 1028 may include code 1030, in one embodiment. As further seen, data storage unit 1028 also includes a trusted storage 1029 to store sensitive information to be protected. Further, an audio I/O 1024 may be coupled to second bus 1020.

Figure 16:
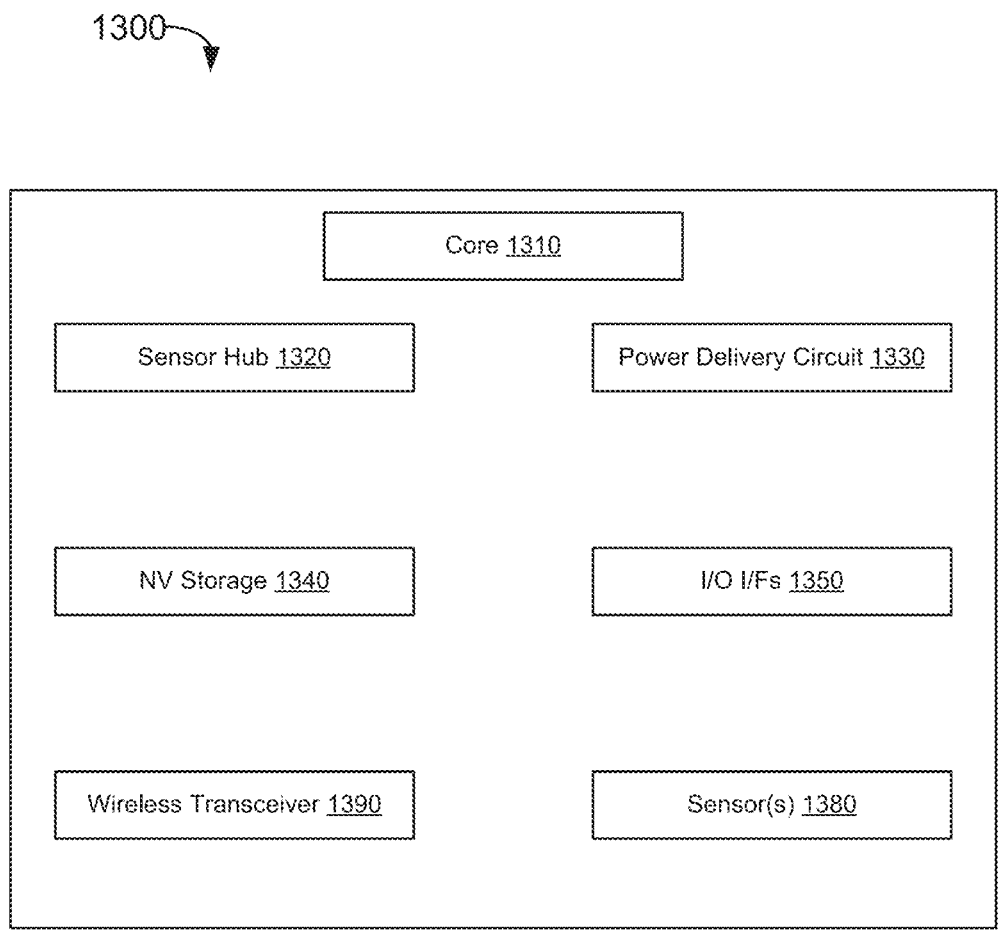

Embodiments may be used in environments where IoT devices may include wearable devices or other small form factor Internet of Things (IoT) devices. Referring now to FIG. 16, shown is a block diagram of a wearable module 1300 in accordance with another embodiment. In one particular implementation, module 1300 may be an Intel® Curie™ module that includes multiple components adapted within a single small module that can be implemented as all or part of a wearable device. As seen, module 1300 includes a core 1310 (of course in other embodiments more than one core may be present). Such core may be a relatively low complexity in-order core, such as based on an Intel Architecture® Quark™ design. In some embodiments, core 1310 may implement a Trusted Execution Environment (TEE). Core 1310 couples to various components including a sensor hub 1320, which may be configured to interact with a plurality of sensors 1380, such as one or more biometric, motion environmental or other sensors. A power delivery circuit 1330 is present, along with a non-volatile storage 1340. In an embodiment, this circuit may include a rechargeable battery and a recharging circuit, which may in one embodiment receive charging power wirelessly. One or more input/output (IO) interfaces 1350, such as one or more interfaces compatible with one or more of USB/SPI/I2C/GPIO protocols, may be present. In addition, a wireless transceiver 1390, which may be a Bluetooth™ low energy or other short-range wireless transceiver is present to enable wireless communications as described herein. Understand that in different implementations a wearable module can take many other forms. Wearable and/or IoT devices have, in comparison with a typical general purpose CPU or a GPU, a small form factor, low power requirements, limited instruction sets, relatively slow computation throughput, or any of the above.

Embodiments may be used in many different types of systems. For example, in one embodiment a communication device can be arranged to perform the various methods and techniques described herein. Of course, the scope of the present invention is not limited to a communication device, and instead other embodiments can be directed to other types of apparatus for processing instructions, or one or more machine readable media including instructions that in response to being executed on a computing device, cause the device to carry out one or more of the methods and techniques described herein.

Program instructions may be used to cause a general-purpose or special-purpose processing system that is programmed with the instructions to perform the operations described herein. Alternatively, the operations may be performed by specific hardware components that contain hard-wired logic for performing the operations, or by any combination of programmed computer components and custom hardware components. The methods described herein may be provided as (a) a computer program product that may include one or more machine readable media having stored thereon instructions that may be used to program a processing system or other electronic device to perform the methods or (b) at least one storage medium having instructions stored thereon for causing a system to perform the methods. The term "machine readable medium" or "storage medium" used herein shall include any medium that is capable of storing or encoding a sequence of instructions (transitory media, including signals, or non-transitory media) for execution by the machine and that cause the machine to perform any one of the methods described herein. The term "machine readable medium" or "storage medium" shall accordingly include, but not be limited to, memories such as solid-state memories, optical and magnetic disks, read-only memory (ROM), programmable ROM (PROM), erasable PROM (EPROM), electrically EPROM (EEPROM), a disk drive, a floppy disk, a compact disk ROM (CD-ROM), a digital versatile disk (DVD), flash memory, a magneto-optical disk, as well as more exotic mediums such as machine-accessible biological state preserving or signal preserving storage. A medium may include any mechanism for storing, transmitting, or receiving information in a form readable by a machine, and the medium may include a medium through which the program code may pass, such as antennas, optical fibers, communications interfaces, and the like. Program code may be transmitted in the form of packets, serial data, parallel data, and the like, and may be used in a compressed or encrypted format. Furthermore, it is common in the art to speak of software, in one form or another (e.g., program, procedure, process, application, module, logic, and so on) as taking an action or causing a result. Such expressions are merely a shorthand way of stating that the execution of the software by a processing system causes the processor to perform an action or produce a result.

A module as used herein refers to any hardware, software, firmware, or a combination thereof. Often module boundaries that are illustrated as separate commonly vary and potentially overlap. For example, a first and a second module may share hardware, software, firmware, or a combination thereof, while potentially retaining some independent hardware, software, or firmware. In one embodiment, use of the term logic includes hardware, such as transistors, registers, or other hardware, such as programmable logic devices. However, in another embodiment, logic also includes software or code integrated with hardware, such as firmware or micro-code.

Example 1 includes a device, comprising: noncontact or minimal contact coupling optics that allow polarized light coupling at two or more wavelengths through the anterior chamber of the eye.

Example 2 includes the device of example 1, wherein the light coupling optics are noncontact and comprise: a manually angle adjustable flat mirror at the input of the eye; a manually adjustable curved mirror at the input of the eye; an automatically electro-optically adjustable flat or curved mirror at the input of the eye; a fixed, manual, or automated angle adjustable flat or curved mirror at the output of the eye for collimation.

Example 3 includes the device of example 2; wherein the mirrors are made of a material with a metallic reflective surface such as silver or gold that accommodates all wavelengths of light from the visible 400 nm to the near infrared 900 nm range, minimizes the effect of aberrations, and maintains the polarization of the beams. This mirrored configuration is not meant to be limiting and as aberration optics become better and more cost effective it is envisioned that the mirrors may be replaced with such transmissive optics.

Example 4 includes the device of example 2, wherein the mirror is approximately 2 mm in diameter to fit on either side of the eye without interfering with the eye lashes or bridge of the nose.

Example 5 includes the device of example 2, wherein the manual adjustment is a screw allowing for coupling at a glancing angle.

Example 6 includes the device of example 2, wherein the automated adjustment is an electro-mechanically piezo device that is controlled by feedback from a detector array or lighted cross hairs target that centers the beam so that the image shows the light impinging on the front and back surfaces of the cornea Example 7 includes the device of example 2; where a beam stop is inserted for the first mirror so the light is not coupled into the back of the eye, keeping it from impinging on the retina.

Example 8 includes the device of example 1, where between the mirrors is a minimal contact scleral or corneal contact lens to index match the beam.

Example 9 includes the device of example 8, where the lens is a donut shape to prevent any visual impairment.

Example 10 includes the device of example 8; where the lens is a soft polymer to prevent discomfort to the patient.

Example 11 includes a system for measuring glucose levels in the aqueous humor of the eye, comprising: two or more light sources configured to generate two or more different wavelength light beams; a polarizer configured to linearly polarize the light beams; a polarization modulation device to modulate a rotation of a plane of polarization of the linearly polarized light beams; coupling optics for coupling the light beams across the anterior chamber of the eye, where the coupling optics could be noncontact and include an input and output flat or concave metallic mirrors made of metallic material that can accommodate visible to near infrared wavelengths, polarized light, and minimize aberrations manual or automated adjustments for the mirrors automated adjustments controlled by a detector array where the coupling optics could be minimal contact and include a scleral or corneal contact lens the lens in a donut shape to minimize visual impairment, a detector unit for receiving the modulated light beam after the modulated light beam is passed through the aqueous humor, the detector unit being configured detect a change in the plane of polarization of the modulated light beam as a result of a concentration of glucose in the aqueous humor.

Example 12 includes the system of example 11, wherein the light coupling optics are noncontact and comprises: a manually angle adjustable flat mirror at the input of the eye; a manually adjustable curved mirror at the input of the eye; an automatically electro-optically adjustable flat or curved mirror at the input of the eye; a fixed, manual, or automated angle adjustable flat or curved mirror at the output of the eye for collimation.

Example 13 includes the system of example 11, wherein the mirrors are made of a material that is a metallic reflective surface such as silver or gold that accommodates all wavelengths of light from the visible 400 nm to the near infrared 900 nm range, minimizes the effect of aberrations, and maintains the polarization of the beams.

This mirrored configuration is not meant to be limiting and as aberration optics become better and more cost effective it is envisioned that the mirrors may be replaced with such transmissive optics. For example, mirrors are not required in all embodiments. Some embodiments may include "non-mirrored" optics (optics with some level of reflection that is less than a mirror) that reflect various beams of light having varying wavelengths, all with introducing an acceptable level of aberration (e.g., distortion, polarization rotation) to the light beams.

An optical aberration is a departure of the performance of an optical system from the predictions of paraxial optics. In an imaging system, it occurs when light from one point of an object does not converge into (or does not diverge from) a single point after transmission through the system. Aberration can occur with different wavelengths and leads to blurring of the image produced by an image-forming optical system. Furthermore, in a lens-based optical propagation system, aberration occurring from different wavelengths propagating through a non-corrected lens can cause the beam to converge or diverge to different points, making a dual wavelength system difficult to collimate.

Example 14 includes the system of example 11, wherein the mirror is approximately 2 mm in diameter to fit on either side of the eye without interfering with the eye lashes or bridge of the nose.

Example 15 includes the system of example 11, whereinvherein the manual adjustment is a screw allowing for coupling at a glancing angle.

Example 16 includes the system of example 11, wherein the automated adjustment is an electro-mechanically piezo device that is controlled by feedback from a detector array or lighted cross hairs target that centers the beam so that the image shows the light impinging on the front and back surfaces of the cornea.

Example 17 includes the system of example 11, where a beam stop is inserted for the first mirror so the light is not coupled into the back of the eye, keeping it from impinging on the retina.

Example 18 includes the system of example 11, where between the mirrors is a minimal contact scleral or corneal contact lens to index match the beam.

Example 19 includes the system of example 11, where the lens is a donut shape to prevent any visual impairment.

Example 20 includes the system of example 11, where the lens is a soft polymer to prevent discomfort to the patient.

Example 21 includes a method for measuring glucose levels in the aqueous humor of the eye, comprising the steps of: generating two or more linearly polarized light beams; passing the light beams through a polarization modulation device to modulate a rotation of a plane of polarization of the linearly polarized light beams; passing the light beams across the anterior chamber of the eye comprising, coupling optics that could be noncontact or minimally contacting and include input and output flat or concave adjustable metallic mirrors a scleral or corneal contact lens; and detecting a change in the plane of polarization of the modulated light beam as a result of a concentration of glucose in the aqueous humor.

Example 22 includes the method of example 21, wherein the mirrors are made of a material that is a metallic reflective surface such as silver or gold that accommodates all wavelengths of light from the visible 400 nm to the near infrared 900 nm range, minimizes the effect of aberrations, and maintains the polarization of the beams. This mirrored configuration is not meant to be limiting and as aberration optics become better and more cost effective it is envisioned that the mirrors may be replaced with such transmissive optics.

Example 23 includes the method of example 21, wherein the mirror is approximately 2 mm in diameter to fit on either side of the eye without interfering with the eye lashes or bridge of the nose.

Example 24 includes the method of example 21, wherein the manual adjustment is a screw allowing for coupling at a glancing angle.

Example 25 includes the method of example 21, wherein the automated adjustment is an electro-mechanically piezo device that is controlled by feedback from a detector array or lighted cross hairs target that centers the beam so that the image shows the light impinging on the front and back surfaces of the cornea.

Example 26 includes the method of example 21, where a beam stop is inserted for the first mirror so the light is not coupled into the back of the eye, keeping it from impinging on the retina.

Example 27 includes the method of example 21, where between the mirrors is a minimal contact scleral or corneal contact lens to index match the beam.

Example 28 includes the method of example 21, where the lens is a donut shape to prevent any visual impairment.

Example 29 includes the method of example 21, where the lens is a soft polymer to prevent discomfort to the patient.

Example 1a includes a system comprising: first and second light sources respectively configured to generate a first light beam having a first wavelength and a second light beam having a second wavelength unequal to the first wavelength; a polarizer configured to linearly polarize the first and second light beams to generate first and second linearly polarized light beams; a polarization modulator to modulate a rotation of a plane of polarization of the first and second linearly polarized light beams to generate first and second modulated light beams; a first mirror configured to receive the first and second modulated light beams and transmit the first and second modulated light beams into a first half of an eye; a second mirror configured to receive first and second phase shifted light beams, which correspond to the first and second modulated light beams, from a second half of the eye and transmit the first and second phase shifted light beams to a signal processor; and the signal processor which is configured to convert the first and second phase shifted light beams into first and second signals; wherein the first and second phase shifted light beams respectively include first and second phase shifts in response to the first and second modulated light beams contacting an analyte in the aqueous humor of the eye.

A polarization modulator may include, for example, a faraday rotator as described in U.S. Pat. No. 6,885,882. The signal processor may include circuitry such photodiodes coupled to a beam splitter (e.g., Wollaston prism) and other components (e.g., lock-in amplifier) described in, for example; U.S. Pat. No. 6,885,882. More generally, the signal processor may include circuitry comprising at least two detectors that receive orthogonal beams and generate a direct current, first harmonic; and second harmonic information for each wavelength that can be used to determine the rotations due to the glucose concentration in the eye (and eliminate or minimize issues pertaining to ambient noise), also described in U.S. Pat. No. 6,885,882.

In an embodiment a single light source could generate multiple light beams at different wavelengths in a non-simultaneous manner. In an embodiment the light source or sources may not be adhered to eye glasses which support the mirrors. For example, the light sources may come from a smart phone which not only produces the light beams but also processes the output to determine phase shift and glucose levels. In some embodiments circuitry like photodiodes are included on the eyeglasses but in other embodiments the photodiodes other light to signal translators) may be included in a smartphone and the like.

Not all embodiments require every component of Example 1A. Some may forego, for example, the polarization modulator. Some may forego, for example, the signal processor (e.g., the processor may be located on a smart phone instead of on eyeglass frames that include the mirrors).

Example 2a includes the system of example 1a wherein at least one of the first and second mirrors includes a concave reflective surface.

Example 3a includes the system of example 2a wherein the concave reflective surface includes a metal.

Example 4a includes the system of example 3a wherein the metal is selected from the group comprising gold and silver.

Example 5a includes the system of example 2a wherein: the first and second wavelengths are both between 400 and 900 nm; and the concave reflective surface includes a material configured to reflect the first and second wavelengths.

Example 6a includes the system of example 2a comprising a third mirror to receive the first and second phase shifted light beams from the second mirror and transmit the first and second phase shifted light beams to the signal processor.

Example 7a includes the system of example 6a comprising a fourth mirror to receive the first and second modulated light beams and transmit the first and second modulated light beams to the first mirror.

Example 8a includes the system of example 2a comprising a third mirror to receive the first and second modulated light beams and transmit the first and second modulated light beams to the first mirror.

Example 9a includes the system of example 8a, wherein at least one the first and third mirrors includes a concave reflective surface and at least another of the first and third mirrors includes a predominantly flat reflective surface.

Example 10a includes the system of example 2a comprising at least one pivot, wherein at least one the first and second mirrors is respectively configured to rotate on the pivot to adjust an angle at which at least one of (a) the first and second modulated light beams are transmitted to the eye, and (b) the first and second phase shifted light beams are received from the eye.

Another version includes the system of example 2a comprising at least one pivot, wherein the first mirror is configured to rotate on the pivot to adjust an angle at which the first and second modulated light beams are transmitted to the eye.

Another version includes the system of example 2a comprising at least one pivot, wherein the second mirror is configured to rotate on the pivot to adjust an angle at which the first and second phase shifted light beams are received from the eye.

Example 11a includes the system of example 10a, comprising: a motor; and a feedback loop; wherein the motor is configured to pivot the at least one the first and second mirrors in response to feedback from the feedback loop.

The system may include a piezo-electric mirror coupled to an image tracking system such as the one described in U.S. Pat. No. 6,885,882.

Example 12a includes the system of example 2a wherein the first mirror is arranged to transmit the first and second modulated light beams into the eye in anterior direction at an angle of between 10 and 20 degrees from a coronal plane that intersects the eye.

Example 13a includes the system of example 12a wherein the second mirror is arranged to receive the first and second phase shifted light beams traveling from the eye in a posterior direction.

Example 14a includes the system of example 12a wherein each of the first and second mirrors is less than 4 mm in diameter.

Example 15a includes the system of example 1a including eye glass frames coupled to the first and second mirrors.

Example 16a includes the system of example 1.5a comprising: a lens coupled to the eye glass frames; and an additional light source configured to transmit a first image onto the lens.

Example 17a includes the system of example 16a wherein the additional light source is configured to transmit the first image onto the lens at a location such that the eye must be focused in a direction selected from group consisting of laterally and medially.

Figure 17A:
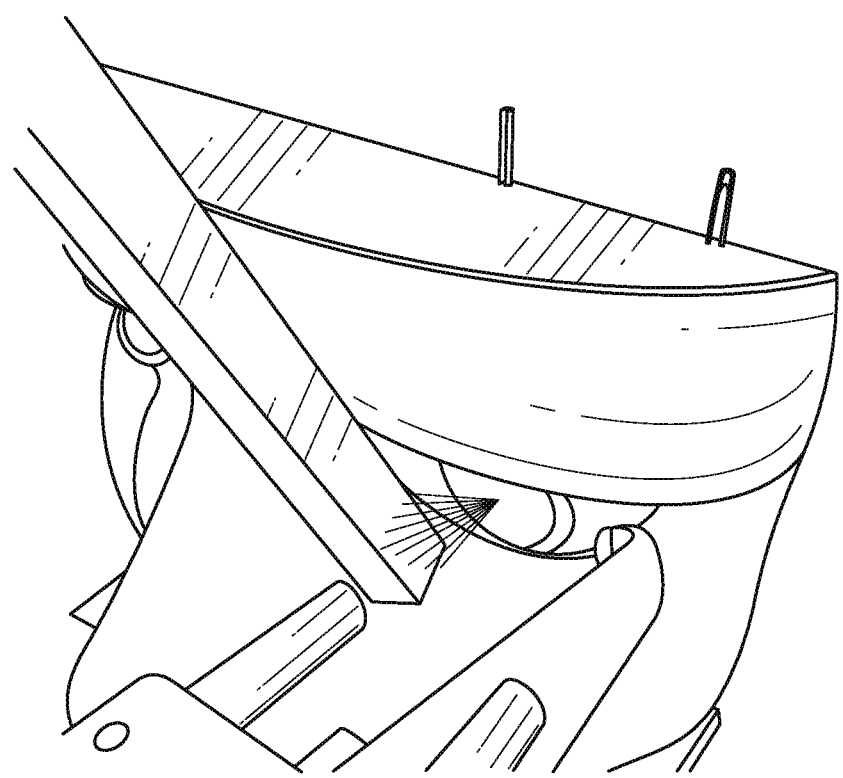
Figure 17B:
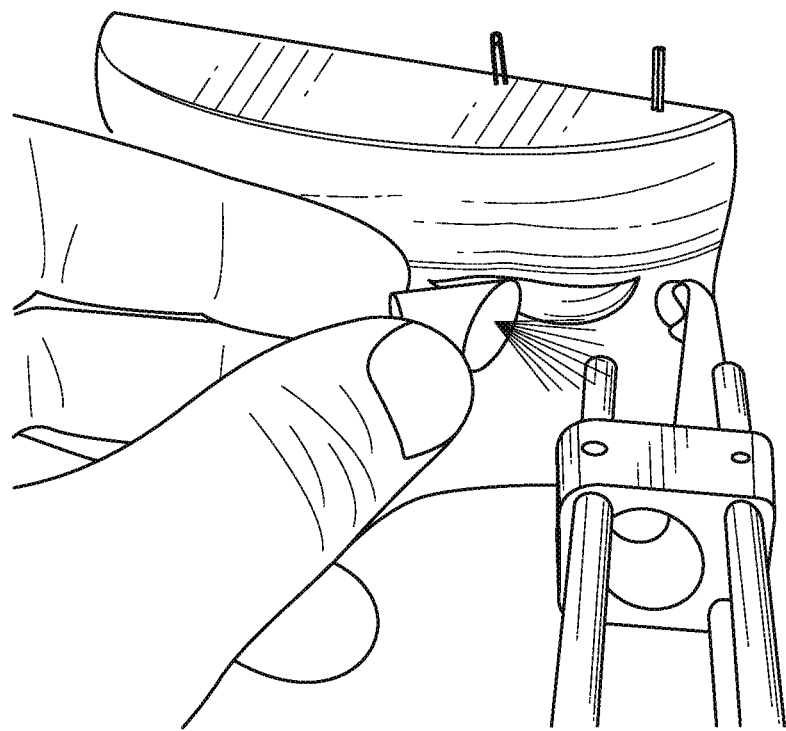

Regarding the eye position, FIGS. 17A and 17B show coupling with the eye looking straight (FIG. 17A) and with the eye off to the side (FIG. 17B). As shown therein, the eye position matters when it comes to being able to couple the light across it. By looking to the side (FIG. 17B), there is more room for the mirror and to get the correct angles to properly couple the light into and out of the eye. This increase in room may make wearables, such as eyeglasses with mirrors coupled thereto more feasible (i.e., more acceptable to human user of the eyeglass frames).

Example 17b includes the system of example 16a wherein the additional light source is configured to transmit the first image onto the lens at a location such that the eye must be focused laterally.

Example 18a the system of example 1a comprising a contact lens configured to match an index of refraction of air with an index of refraction of tissue of the eye.

Example 19a includes a system comprising: first and second light sources respectively configured to generate a first light beam having a first wavelength and a second light beam having a second wavelength unequal to the first wavelength; a polarizer configured to linearly polarize the first and second light beams to generate first and second linearly polarized light beams; a polarization modulator to modulate a rotation of a plane of polarization of each of the first and second linearly polarized light beams to generate first and second modulated light beams; a first mirror oriented to receive the first and second modulated light beams and transmit the first and second modulated light beams into a first half of an eye and across the eye without being directed towards a retina of the eye; a second mirror configured to receive first and second phase shifted light beams, which correspond to the first and second modulated light beams, from a second half of the eye and transmit the first and second phase shifted light beams to a signal processor; and the signal processor which is configured to convert the first and second phase shifted light beams into first and second signals; wherein the first and second phase shifted light beams respectively include first and second phase shifts in response to the first and second modulated light beams contacting an analyte in an aqueous humor of the eye; wherein the system does not include an index matching medium to index match between air and the eye.

Example 20a includes the system of example 19a wherein at least one of the first and second mirrors includes a concave reflective surface.

It is to be understood that the above description and examples are intended to be illustrative, and not restrictive. For example, the above-described embodiments may be used in combination with each other. Many other embodiments will be apparent to those of skill in the art upon reviewing the above description. The scope of the invention therefore should be determined with reference to the appended claims, along with the full scope of equivalents to which such claims are entitled.

What is claimed is:

1. A system comprising:
   first and second light sources respectively configured to generate a first light beam from the first light source having a first wavelength and a second light beam from the second light source having a second wavelength unequal to the first wavelength;
   a polarizer configured to linearly polarize the first and second light beams to generate first and second linearly polarized light beams;
   a polarization modulator to modulate a rotation of a plane of polarization of each of the first and second linearly polarized light beams to generate first and second modulated light beams;
   a first mirror configured to receive the first and second modulated light beams and transmit the first and second modulated light beams into a first half of an eye;
   a second mirror configured to receive first and second phase shifted light beams, which correspond to the first and second modulated light beams, from a second half of the eye;
   a signal processor configured to receive the first and second phase shifted light beams and configured to convert the first and second phase shifted light beams into first and second signals;
   wherein the first mirror is adjustable for alignment and the second mirror has a concave reflective surface; and
   wherein the first and second phase shifted light beams respectively include first and second phase shifts in response to the first and second modulated light beams contacting an analyte in an aqueous humor of the eye.

2. The system of claim 1 wherein the concave reflective surface includes a metal.

3. The system of claim 2 wherein the metal is selected from the group comprising gold and silver.

4. The system of claim 1 wherein: the first and second wavelengths are both between 400 and 900 nm; and the concave reflective surface includes a material configured to reflect the first and second wavelengths.

5. The system of claim 1 comprising a third mirror to receive the first and second phase shifted light beams from the second mirror and transmit the first and second phase shifted light beams to the signal processor.

6. The system of claim 5 comprising a fourth mirror to receive the first and second modulated light beams and transmit the first and second modulated light beams to the first mirror.

7. The system of claim 1 comprising a third mirror to receive the first and second modulated light beams and transmit the first and second modulated light beams to the first mirror.

8. The system of claim 7, wherein at least one the first and third mirrors includes a concave reflective surface and at least another of the first and third mirrors includes a predominantly a reflective surface.

9. The system of claim 1; wherein at least one the first and second mirrors is respectively configured to rotate to adjust an angle at which at least one of (a) the first and second modulated light beams are transmitted to the eye, and (b) the first and second phase shifted light beams are received from the eye.

10. The system of claim 9, comprising: a motor; and a feedback loop; wherein the motor is configured to pivot the at least one the first and second mirrors in response to feedback from the feedback loop.

11. The system of claim 1 wherein the first mirror is arranged to transmit the first and second modulated light beams into the eye in an anterior direction at an angle of between 10 and 20 degrees from a coronal plane that intersects the eye.

12. The system of claim 11 wherein the second mirror is arranged to receive the first and second phase shifted light beams traveling from the eye in a posterior direction.

13. The system of claim 11 wherein each of the first and second mirrors is less than 4 mm in diameter.

14. The system of claim 1 including eye glass frames coupled to the first and second mirrors.

15. The system of claim 14 comprising: a lens coupled to the eye glass frames; and an additional light source configured to transmit a first image onto the lens.

16. The system of claim 15 wherein the additional light source is configured to transmit the first image onto the lens at a location such that the eye must be focused in a direction selected from group consisting of laterally and medially.

17. The system of claim 1 comprising a contact lens configured to be placed upon the eye and so that the first and second modulated light beams from the first mirror pass through the contact lens to match an index of refraction of air with an index of refraction of tissue of the eye.

* * * * *